United States Patent
Liu et al.

(10) Patent No.: US 12,129,496 B2
(45) Date of Patent: Oct. 29, 2024

(54) HAPLOTYPE-BASED TREATMENT OF RP1 ASSOCIATED RETINAL DEGENERATIONS

(71) Applicant: Massachusetts Eye and Ear Infirmary, Boston, MA (US)

(72) Inventors: Qin Liu, Boston, MA (US); Caitlin Collin, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 235 days.

(21) Appl. No.: 17/175,234

(22) Filed: Feb. 12, 2021

(65) Prior Publication Data

US 2021/0269783 A1    Sep. 2, 2021

Related U.S. Application Data

(60) Provisional application No. 62/975,636, filed on Feb. 12, 2020.

(51) Int. Cl.
| | | |
|---|---|---|
| *C12N 9/22* | (2006.01) | |
| *A61K 9/00* | (2006.01) | |
| *A61K 38/16* | (2006.01) | |
| *C12N 15/11* | (2006.01) | |
| *C12N 15/90* | (2006.01) | |
| *A61K 38/00* | (2006.01) | |

(52) U.S. Cl.
CPC .............. *C12N 9/22* (2013.01); *A61K 9/0048* (2013.01); *A61K 38/164* (2013.01); *C12N 15/11* (2013.01); *C12N 15/907* (2013.01); *A61K 38/00* (2013.01); *C12N 2310/20* (2017.05); *C12N 2800/80* (2013.01)

(58) Field of Classification Search
CPC ...... C12N 9/22; C12N 15/11; C12N 2310/20; C12N 2800/80; C12N 2320/34; A61K 9/0048
See application file for complete search history.

(56) References Cited

U.S. PATENT DOCUMENTS

| | | | |
|---|---|---|---|
| 4,868,116 A | 9/1989 | Morgan et al. | |
| 4,980,286 A | 12/1990 | Morgan et al. | |
| 2019/0010481 A1 | 1/2019 | Joung et al. | |
| 2019/0345501 A1 | 11/2019 | Nielsen et al. | |
| 2021/0017509 A1* | 1/2021 | Wu | C12N 9/16 |

FOREIGN PATENT DOCUMENTS

| | | |
|---|---|---|
| EP | 0043075 | 1/1982 |
| JP | S 57124055 | 8/1982 |
| WO | WO 89/02468 | 2/1988 |
| WO | WO 89/05345 | 6/1989 |
| WO | WO 89/07136 | 8/1989 |
| WO | WO 91/06309 | 5/1991 |
| WO | WO 92/07573 | 5/1992 |
| WO | WO 2014/144592 | 9/2014 |
| WO | WO 2015/054653 | 4/2015 |
| WO | WO 2016/141224 | 9/2016 |
| WO | WO 2017/040348 | 3/2017 |
| WO | WO 2018/026976 | 2/2018 |
| WO | WO 2019/165322 | 8/2019 |
| WO | WO 2019/183630 | 9/2019 |
| WO | WO 2019/183641 | 9/2019 |

OTHER PUBLICATIONS

NCBI Variation Viewer for RP1 (Year: 2015).*
Graham et al.(Resources for the design of CRISPR gene editing experiments. Genome Biology, vol. 16, Nov. 2015). ( Year: 2015).*
UCSC HapMap SNP Viewer for RP1 (Genome browser accessible through genome.ucsc.edu for RP1 gene wherein Hap Map viewer can be selected under 'configure' tracks and selecting HapMap SNPs (Year: 2015).*
A global reference for human genetic variation: The 1000 Genomes Project Consortium, Nature, vol. 526, Sep. 2015). ( Year: 2015).*
Acland et al., "Long-Term Restoration of Rod and Cone Vision by Single Dose rAAV-Mediated Gene Transfer to the Retina in a Canine Model of Childhood Blindness," Mol. Ther., Dec. 2005, 12(6):1072-1082.
Alexander and Hauswirth, "Adeno-associated viral vectors and the retina," Adv. Exp. Med. Biol., Jan. 2008, 613:121-128.
Alexopoulou et al., "The CMV early enhancer/chicken β actin (CAG) promoter can be used to drive transgene expression during the differentiation of murine embryonic stem cells into vascular progenitors," BMC Cell. Biol., Dec. 2008, 9(1)-1.
Allocca et al., "Novel Adeno-Associated Virus Serotypes Efficiently Transduce Murine Photoreceptors," J. Virol., Oct. 2007, 81(20):11372-11380.
Armentano et al., "Expression of human factor IX in rabbit hepatocytes by retrovirus-mediated gene transfer: potential for gene therapy of hemophilia B," Proc. Natl. Acad. Sci. USA, Aug. 1990, 87(16):6141-6145.
Asokan et al., "The AAV vector toolkit: poised at the clinical crossroads," Mol Ther., Apr. 2012, 20(4):699-708.
Bainbridge et al., "Effect of gene therapy on visual function in Leber's congenital amaurosis," N. Engl. J. Med., May 2008, 358(21):2231-2239.
Bennett et al., "AAV2 Gene Therapy Readministration in Three Adults with Congenital Blindness," Science Translational Medicine, Feb. 2012, 4(120):ra15.
Berkner et al., "Development of adenovirus vectors for the expression of heterologous genes," BioTechniques, Jul.-Aug. 1988, 6(7):616-629.
Berson et al., "Clinical features and mutations in patients with dominant retinitis pigmentosa-1 (RP1)," Investigative Ophthalmology & Visual Science, Oct. 2001, 42(10):2217-2224.

(Continued)

*Primary Examiner* — Valarie E Bertoglio
*Assistant Examiner* — Matasha Dhar
(74) *Attorney, Agent, or Firm* — Fish & Richardson P.C.

(57) ABSTRACT

Methods and compositions for the use of CRISPR/Cas9 technology for treating RP1 mutation-associated autosomal dominant Retinitis Pigmentosa (adRP).

13 Claims, 7 Drawing Sheets

Specification includes a Sequence Listing.

(56) References Cited

OTHER PUBLICATIONS

Beusechem et al., "Long-term expression of human adenosine deaminase in rhesus monkeys transplanted with retrovirus-infected bone-marrow cells," Proc. Natl. Acad. Sci. USA, Aug. 1992, 89(16):7640-7644.

Boye et al., "A comprehensive review of retinal gene therapy," Mol. Ther., Mar. 2013, 21(3):509-519.

Casini et al., "A highly specific SpCas9 variant is identified by in vivo screening in yeast," Nat. Biotechnol., Mar. 2018, 36(3):265-271.

Chen et al., "Compound heterozygosity of two novel truncation mutations in RP1 causing autosomal recessive retinitis pigmentosa," Invest. Ophthalmol. Vis.Sci., Nov. 2009, 51(4):2236-2242.

Chen et al., "Enhanced proofreading governs CRISPR-Cas9 targeting accuracy," Nature, Oct. 2017, 550(7676):407-410.

Cho et al., "Targeted genome engineering in human cells with the Cas9 RNA-guided endonuclease," Nat. Biotechnol., Mar. 2013, 31(3):230-232.

Chowdhury et al., "Long-term Improvement of Hypercholesterolemia After Ex Vivo Gene Therapy in LDLR-deficient Rabbits," Science, Dec. 1991, 254(5039):1802-1805.

Cideciyan et al., "Vision 1 Year after Gene Therapy for Leber's Congenital Amaurosis," N. Engl. J. Med., 361(7):725-727.

Cideciyan et al., "Human gene therapy for RPE65 isomerase deficiency activates the retinoid cycle of vision but with slow rod kinetics," Proc. Natl. Acad. Sci. USA, 105(39):15112-15117.

Cokol et al., "Finding nuclear localization signals," EMBO Rep. Nov. 2000, 1(5):411-415.

Cong et al., "Multiplex genome engineering using CRISPR/Cas systems," Science, Feb. 2013, 339(6121):819-823.

Dahlman et al., "Orthogonal gene knockout and activation with a catalytically active Cas9 nuclease," Nat. Biotechnol., Nov. 2015, 33(11):1159-1161.

Dai et al., "Gene therapy via primary myoblasts: long-term expression of factor IX protein following transplantation in vivo," Proc. Natl. Acad. Sci. USA, Nov. 1992, 89(22):10892-10895.

Danos and Mulligan, "Safe and efficient generation of recombinant retroviruses with amphotropic and ecotropic host ranges," Proc. Natl. Acad. Sci. USA, Sep. 1988, 85(17):6460-6464.

Deyle and Russell, "Adeno-associated virus vector integration," Curr Opin Mol Ther., Aug. 2009, 11(4):442-447.

Dicarlo et al., "Genome engineering in Saccharomyces cerevisiae using CRISPR-Cas systems," Nucleic Acids Res., Apr. 2013, 41(7):4336-4343.

Dinculescu et al., "Adeno-associated virus-vectored gene therapy for retinal disease," Hum. Gene Ther., Jun. 2005, 16(6):649-663.

Domenger and Grimm, "Next-generation AAV vectors-do not judge a virus (only) by its cover," Human Molecular Genetics, Oct. 2019, 28(R1):R3-R14.

Eglitis, et al., "Gene expression in mice after high efficiency retroviral-mediated gene transfer," Science, Dec. 1985, 230(4732):1395-1398.

Esumi et al., "Analysis of the VMD2 promoter and implication of E-box binding factors in its regulation," Journal Biological Chemistry, Apr. 2004, 279(18):19064-19073.

Fagerlund et al., "The Cpf1 CRISPR-Cas protein expands genome-editing tools," Genome Biol., Dec. 2015, 16(1)251.

Ferry et al., "Retroviral-mediated gene transfer into hepatocytes in vivo," Proc. Natl. Acad. Sci. USA, Oct. 1999, 88(19):8377-8381.

Flotte et al., "Expression of the cystic fibrosis transmembrane conductance regulator from a novel adeno-associated virus promoter," J. Biol. Chem., Feb. 1993, 268(5):3781-3790.

Flotte et al., "Gene expression from adeno-associated virus vectors in airway epithelial cells," Am. J. Respir. Cell. Mol. Biol., Sep. 1992, 7(3):349-356.

Freitas and Cunha, "Mechanisms and Signals for the Nuclear Import of Proteins," Curr Genomics. Dec. 10(8): 550-557.

Fu et al., "Targeted genome editing in human cells using CRISPR/Cas nucleases and truncated guide RNAs," Methods Enzymol., Jan. 2014, 546:21-45.

Gamundi et al., "Three novel and the common Arg677Ter RP1 protein truncating mutations causing autosomal dominant retinitis pigmentosa in a Spanish population," BMC.Med.Genet., Dec. 2006, 7(1)35, 10 pages.

Gandra et al., "Retinitis pigmentosa: mutation analysis of RHO, PRPF31, RP1, and IMPDH1 genes in patients from Indial," Mol. Vis., Jun. 2008, 14:1105-1113.

Gray et al., "Optimizing promoters for recombinant adeno-associated virus-mediated gene expression in the peripheral and central nervous system using self-complementary vectors," Hum. Gene. Ther,. Sep. 2011, 22(9):1143-1153.

Guziewicz et al., "Recombinant AAV-mediated BEST1 transfer to the retinal pigment epithelium: analysis of serotype-dependent retinal effects, " PLoS One, Oct. 2013, 8(10):e75666.

Haj-Ahmand and Graham, "Development of a helper-independent human adenovirus vector and its use in the transfer of the herpes simplex virus thymidine kinase gene," J. Virol., Jan. 1986, 57(1):267-274.

Hauswirth et al., "Treatment of leber congenital amaurosis due to RPE65 mutations by ocular subretinal injection of adeno-associated virus gene vector: short-term results of a phase I trial," Hum. Gene. Ther., Oct. 2008, 19(10):979-990.

Hermonat et al., "Use of adeno-associated virus as a mammalian DNA cloning vector: transduction of neomycin resistance into mammalian tissue culture cells," Proc. Natl. Acad. Sci. USA, Oct. 1984, 81(20):6466-6470.

Hu et al., "Evolved Cas9 variants with broad PAM compatibility and high DNA specificity," Nature, Apr. 2018, 556(7699):57-63.

Huber et al., "Retroviral-mediated gene therapy for the treatment of hepatocellular carcinoma: an innovative approach for cancer therapy," Proc. Natl. Acad. Sci. USA, Sep. 1991, 88(18):8039-8043.

Hwang et al., "Efficient genome editing in zebrafish using a CRISPR-Cas system," Nat. Biotechnol., Jan. 2013, 31(3):227-229.

Hwang et al., "Targeted mutagenesis in zebrafish using CRISPR RNA-guided nucleases," Methods Mol. Biol., Jan. 2015, 1311:317-34.

Hwu et al., "Functional and molecular characterization of tumor-infiltrating lymphocytes transduced with tumor necrosis factor-alpha cDNA for the gene therapy of cancer in humans," J. Immunol., 150(9):4104-4115.

Jacobson et al., "Disease expression of RP1 mutations causing autosomal dominant retinitis pigmentosa," Investigative Ophthalmology & Visual Science, Jun. 2000, 41(7):1898-908.

Jacobson et al., "Gene Therapy for Leber Congenital Amaurosis caused by RPE65 mutations: Safety and Efficacy in Fifteen Children and Adults Followed up to Three Years," Archives Ophthalmology, 130:9-24.

Jiang et al., "RNA-guided editing of bacterial genomes using CRISPR-Cas systems," Nat. Biotechnol., Mar. 2013, 31(3):233-239.

Jinek et al., "A programmable dual-RNA-guided DNA endonuclease in adaptive bacterial immunity," Aug. 2012, Science, 337(6096):816-821.

Jinek et al., "RNA-programmed genome editing in human cells," eLife, Jan. 2013, 2:e00471, 9 pages.

Katz et al., "Gene therapy delivery systems for enhancing viral and nonviral vectors for cardiac diseases: current concepts and future applications," Human Gene Therapy, Nov. 2013, 24:914.

Kay et al., "Hepatic gene therapy: persistent expression of human al-antitrypsin in mice after direct gene delivery in vivo," Human Gene Therapy, Dec. 1992, 3(6):641-647.

Kim et al., "Highly efficient RNA-guided genome editing in human cells via delivery of purified Cas9 ribonucleoproteins," Genome Research, Jun. 2014, 24(6):1012-1019.

Kleinstiver et al., "Broadening the targeting range of Staphylococcus aureus CRISPR-Cas9 by modifying PAM recognition," Nat. Biotechnol., Dec. 2015, 33(12):1293-1298.

Kleinstiver et al., "Engineered CRISPR-Cas9 nucleases with altered PAM specificities," Nature, Jul. 2015, 523(7561):481-485.

Kleinstiver et al., "Genome-wide specificities of CRISPR-Cas Cpf1 nucleases in human," Nat. Biotechnol., Aug. 2016, 34(8):869-874.

(56) References Cited

OTHER PUBLICATIONS

Kleinstiver et al., "High-fidelity CRISPR-Cas9 nucleases with no detectable genome-wide off-target effects," Nature, Jan. 2016, 529(7587):490-495.
Konermann et al., "Genome-scale transcriptional activation by an engineered CRISPR-Cas9 complex," Nature, Jan. 2015, 517(7536):583-588.
Le Meur et al., "Restoration of vision in RPE65-deficient Briard dogs using an AAV serotype 4 vector that specifically targets the retinal pigmented epithelium," Gene Ther., Feb. 2007, 14(4):292-303.
Lee et al., "Directed evolution of CRISPR-Cas9 to increase its specificity," Nat. Commun., Aug. 2018, 9(1):3048.
Leung et al., "Dissection of the karyopherin $\alpha$ nuclear localization signal (NLS)-binding groove: functional requirements for NLS binding," Journal of Biol. Chem., Oct. 2003, 278(43):41947-41953.
Lewin et al., "Ribozyme rescue of photoreceptor cells in a transgenic rat model of autosomal dominant retinitis pigmentosa," Nat. Med., Aug. 1998, 4(8):967-971.
Liang et al., "Rapid and highly efficient mammalian cell engineering via Cas9 protein transfection," Journal of Biotechnology, Aug. 2015, 208:44-53.
Liu et al., "Expression of wild-type Rp1 protein in Rp1 knock-in mice rescues the retinal degeneration phenotype," PLoS One, Aug. 2012, 7(8):e43251.
Liu et al., "The retinitis pigmentosa 1 protein is a photoreceptor microtubule-associated protein," J. Neurosci., Jul. 2004, 24(29):6427-6436.
Liu et al., "The severity of retinal degeneration in Rp1h gene-targeted mice is dependent on genetic background," Investigative Ophthalmology & Visual Science, Apr. 2009, 50(4):1566-1574.
MacLaren et al., "Retinal gene therapy in patients with choroideremia: initial findings from a phase 1/2 clinical trial," Lancet., Mar. 2014, 383(9923):1129-1137.
Maguire et al., "Age-dependent effects of RPE65 gene therapy for Leber's congenital amaurosis: a phase 1 dose-escalation trial," Lancet., Nov. 2009, 374(9701):1597-1605.
Maguire et al., "Safety and efficacy of gene transfer for Leber's congenital amaurosis," N. Engl. J. Med., May 2008, 358(21):2240-2248.
Makarova et al., "An updated evolutionary classification of CRISPR-Cas systems," Nat. Rev. Microbiol., Nov. 2015, 13(11):722-736.
Mali et al., "RNA-guided human genome engineering via Cas9," Science, Feb. 2013, 339(6121):823-826.
McLaughlin et al., "Adeno-associated virus general transduction vectors: analysis of proviral structures," J. Virol. Jun. 1988, 62(6):1963-1973.
Mingozzi and High, "Therapeutic in vivo gene transfer for genetic disease using AAV: progress and challenges," Nature Reviews Genetics, May 2011, 12(5):341-355.
Mizuno et al., "Basic research for interferon gene therapy against malignant glioma," No Shinkei Geka, 20(5):547-551 (5 pages with English abstract).
Muzyczka et al., "Use of adeno-associated virus as a general transduction vector for mammalian cells," Curr. Topics in Micro and Immunol., 1992, 158:97-129.
Nishimasu et al., "Engineered CRISPR-Cas9 nuclease with expanded targeting space," Science, Sep. 2018, 361(6408):1259-1262.
O'Reilly et al., "A transgenic mouse model for gene therapy of rhodopsin-linked Retinitis Pigmentosa," Vision Research, Feb. 2008, 48(3):386-391.
O'Reilly et al., "RNA interference-mediated suppression and replacement of human rhodopsin in vivo," American Journal of Human Genetics, Jul. 2007, 81(1):127-135.
Osborn et al., "Fanconi anemia gene editing by the CRISPR/Cas9 system," Hum. Gene Ther., Feb. 2015, 26(2): 114-126.
Pratt and Jordan, "Ia inhibitory interneurons and Renshaw cells as contributors to the spinal mechanisms of fictive locomotion," J Neurophysiology 1987, 57 (1), 56-71.
Ran et al., "In vivo genome editing using *Staphylococcus aureus* Cas9," Nature, Apr. 2015. 520(7546):186-191.
Rosenfeld et al., "In vivo transfer of the human cystic fibrosis transmembrane conductance regulator gene to the airway epithelium," Cell, Jan. 1992, 68(1):143-155.
Rosenfeld et al., "Adenovirus-mediated transfer of a recombinant alpha 1-antitrypsin gene to the lung epithelium in vivo," Science, Apr. 1991, 252(5004):431-434.
Samulski et al., "Helper-free stocks of recombinant adeno-associated viruses: normal integration does not require viral gene expression," J. Virol., Sep. 1989, 63(9):3822-3828.
Schunder et al., "First indication for a Functional CRISPR/Cas system in Francisella tularensis," Int. J. Med. Microbiol., Mar. 2013, 303(2):51-60.
Schwartz et al., "De Novo Mutation in the RP1 Gene (Arg677ter) Associated with Retinitis Pigmentosa," Investigative Ophthalmology & Visual Science, Aug. 2003, 44(8):3593-3597.
Shen et al., "Generation of gene-modified mice via Cas9/RNA-mediated gene targeting," Cell Res., May 2013, 23(5):720-723.
Shmakov et al., "Discovery and Functional Characterization of Diverse Class 2 CRISPR-Cas Systems," Mol. Cell., Nov. 2015, 60(3):385-397.
Simonelli et al., "Gene therapy for Leber's congenital amaurosis is safe and effective through 1.5 years after vector administration," Mol. Ther., 18(3):643-650.
Slaymaker et al., "Rationally engineered Cas9 nucleases with improved specificity," Science, Jan. 2016, 351(6268):84-88.
Stieger et al., "Subretinal delivery of recombinant AAV serotype 8 vector in dogs results in gene transfer to neurons in the brain," Mol. Ther., May 2008, 16(5):916-923.
Swiech et al., "In vivo interrogation of gene function in the mammalian brain using CRISPR-Cas9," Nat. Biotechnol., Jan. 2015, 33(1):102-106.
Tabebordbar et al., "In vivo gene editing in dystrophic mouse muscle and muscle stem cells," Science, Jan. 2016, 351(6271):407-411.
Tratschin et al., "A human parvovirus, adeno-associated virus, as a eucaryotic vector: transient expression and encapsidation of the procaryotic gene for chloramphenicol acetyl-transferase," Mol. Cell. Biol., Oct. 1984, 4(10):2072-2081.
Tratschin et al., "Genetic analysis of adeno-associated virus: properties of deletion mutants constructed in vitro and evidence for an adeno-associated virus replication function," J. Virol., Sep. 1984, 51(3):611-619.
Tsai and Joung, "Defining and improving the genome-wide specificities of CRISPR-Cas9 nucleases," Nat. Rev. Genet., May 2016, 17(5):300-312.
Tsai et al., "Dimeric CRISPR RNA-guided FokI nucleases for highly specific genome editing," Nat. Biotechnol., Jun. 2014, 32(6):569-576.
Vakulskas et al., "A high-fidelity Cas9 mutant delivered as a ribonucleoprotein complex enables efficient gene editing in human hematopoietic stem and progenitor cells," Nat. Med., Aug. 2018, 24(8):1216-1224.
Vandenberghe and Auricchio, "Novel adeno-associated viral vectors for retinal gene therapy," Gene Therapy., Feb. 2012, 19(2):162-168.
Vandenberghe et al., "Dosage thresholds for AAV2 and AAV8 photoreceptor gene therapy in monkey," Sci. Transl. Med., Jun. 2011, 3(88):88ra54, 11 pages.
Vandenberghe et al., "AAV9 Targets Cone Photoreceptors in the Nonhuman Primate Retina," PLoS One. Jan. 2013, 8:e53463, 7 pages.
Wen et al., "Overexpression of rhodopsin alters the structure and photoresponse of rod photoreceptors," Biophys. J., Feb. 2009, 96(3):939-950.
Wilson et al., "Retrovirus-mediated transduction of adult hepatocytes," Proc. Natl. Acad. Sci. USA, May 1988, 85(9):3014-3018.
Wondisford et al., "Cloning of the human thyrotropin $\beta$-subunit gene and transient expression of biologically active human thyrotropin after gene transfection," Mol. Endocrinol., Jan. 1988, 2(1):32-39.
Wyvekens et al., "Dimeric CRISPR RNA-Guided FokI-dCas9 Nucleases Directed by Truncated gRNAs for Highly Specific Genome Editing," Hum. Gene. Ther., Jul. 2015, 26(7):425-431.

(56) References Cited

OTHER PUBLICATIONS

Yang et al., "A dual AAV system enables the Cas9-mediated correction of a metabolic liver disease in newborn mice," Nature Biotechnology, Mar. 2016, 34(3):334-338.

Yin et al., "Genome editing with Cas9 in adult mice corrects a disease mutation and phenotype," Nat. Biotechnol., Jun. 2014, 32(6):551-553.

Zetsche et al., "Cpf1 is a single RNA-guided endonuclease of a class 2 CRISPR-Cas system," Cell, Oct. 2015, 163(3):759-771.

Zuris et al., "Cationic lipid-mediated delivery of proteins enables efficient protein-based genome editing in vitro and in vivo," Nature Biotechnology, Jan. 2015, 33(1):73-80.

International Preliminary Report on Patentability in International Appln. No. PCT/US2021/017942, mailed on Aug. 11, 2022, 10 pages.

International Search Report and Written Opinion in International Appln. No. PCT/US2021/017942, dated Jul. 22, 2021, 14 pages.

Bowne et al., "Mutations in the RP1 gene causing autosomal dominant retinitis pigmentosa," Hum Mol Genet., Oct. 1999, 8(11):2121-2128.

Office Action in Canadian Appln. No. 3,169,991, dated Nov. 9, 2023, 4 pages.

Extended European Search Report in European Appln. No. 21753483.3, dated Feb. 16, 2024, 7 pages.

Ma et al., "Identification of a novel p. R1443W mutation in RP1 gene associated with retinitis pigmentosa sine pigmento," Int J Ophthalmol., Aug. 2013, 6(4):430-435.

* cited by examiner

HAPLOTYPE-BASED TREATMENT OF RP1 ASSOCIATED RETINAL DEGENERATIONS

CROSS-REFERENCE TO RELATED APPLICATIONS

This application claims priority and benefit from U.S. Provisional Patent Application 62/975,636, filed Feb. 12, 2020. The entire contents and disclosure of the foregoing are incorporated herein by reference.

SEQUENCE LISTING

The instant application contains a Sequence Listing which has been submitted electronically in ASCII format and is hereby incorporated by reference in its entirety. Said ASCII copy, created on Mar. 24, 2021, is named SequenceListing and is 24,576 bytes in size.

TECHNICAL FIELD

Described herein are methods and compositions for the use of CRISPR/Cas9 technology for treating retinitis pigmentosa 1 protein (RP1) mutation-associated autosomal dominant Retinitis Pigmentosa (adRP).

BACKGROUND

Retinitis pigmentosa (RP) is an important cause of vision loss for people of all ages. As a group, these diseases are characterized by the progressive death of the light sensitive photoreceptor cells of the retina, which are required for vision. RP is highly heterogeneous genetically, and mutations in the RP genes can be passed from parent to offspring in multiple genetic inheritance modes—autosomal recessive, autosomal dominant, or X-linked. Currently, mutations in more than 60 genes are known to cause non-syndromic RP, and mutations in an additional 73 genes cause syndromic forms of RP, such as Usher syndrome and Bardet-Biedl syndrome. For recessive forms of RP, significant progress has been made in developing gene augmentation therapy, in which supplementing retinal cells with a normal copy of the disease gene can have a therapeutic effect. However, no effective therapy has been developed for dominant RP, which accounts for ~40% of all RP cases. Most dominant RP genes produce a mutant protein that damages cells, rendering gene augmentation therapy ineffective. A permanent cure for a dominant RP, or any dominant form of inherited retinal degenerations (IRDs), therefore requires correcting or suppressing the production of the mutant protein.

SUMMARY

CRISPR/Cas9 (Clustered Regularly Interspaced Short Palindromic Repeat-associated protein 9) genome editing technology has been shown to be an efficient tool for editing the genetic code in mammalian cells and many organisms. Described herein are methods for the specific abolishment of the mutant copy of dominant RP genes via CRISPR/Cas9 system to eliminate the production of pathogenic proteins, and thus prevent photoreceptor cell death in dominant RP patients. Thus described herein is the use of CRISPR/Cas9 technology for treating RP1 mutation-associated autosomal dominant Retinitis Pigmentosa (adRP).

Thus, provided herein are nucleic acids comprising sequences encoding a Cas9 protein, and a first guide RNA (gRNA), and a second gRNA, wherein the first and/or second RNAs are targeted to sequences comprising single nucleotide polymorphisms (SNPs) in a mutated allele of a RP1 gene of a subject, wherein the mutated allele is associated with autosomal dominant retinitis pigmentosa (adRP). In some embodiments, the first gRNA comprises a target sequence in intron 1 or 3, and/or wherein the second gRNA comprises a target sequence in intron 3 or exon 4, preferably wherein one or both gRNAs comprise a sequence shown in Table 6. In some embodiments, the first or second gRNAs are targeted to bi-allelic sequences, e.g., in intron 3, while the other gRNA is targeted to a sequence comprising a SNP.

Also provided herein are nucleic acids comprising sequences encoding a Cas9 protein, and optionally at least one gRNA targeted to a sequence comprising a single nucleotide polymorphism (SNP) in intron 1 or 3 or exon 4, and optionally comprising a sequence encoding a second gRNA, optionally wherein the first and second gRNAs targeted to sequences in intron 1 or 3 and/or in intron 3 or exon 4, wherein the second gRNA is targeted to a bi-allelic sequence or sequence comprising a SNP of an RP1 gene of a human subject. In some embodiments, the gRNA comprises a target sequence shown in Table 6.

In some embodiments, the nucleic acids encodes *S. aureus* Cas9 or *S. pyogenes* Cas9.

In some embodiments, the Cas9 comprises a nuclear localization signal, optionally a C-terminal nuclear localization signal and/or an N-terminal nuclear localization signal; and/or wherein the sequences encoding Cas9 comprises a polyadenylation signal.

In some embodiments, the gRNA is a unimolecular *S. aureus* gRNA comprising SEQ ID NO: 1 or SEQ ID NO: 2 (which correspond to SEQ ID NO: 7 or SEQ ID NO: 8 of WO 2018/026976 respectively), or the corresponding two-part modular *S. aureus* gRNA, wherein the crRNA component comprises SEQ ID NO: 3 or SEQ ID NO: 4 (the bold section of SEQ ID NO: 1 or SEQ ID NO: 2) and the tracrRNA component comprises SEQ ID NO: 5 or SEQ ID NO: 6 (the underlined section of SEQ ID NO: 1 or SEQ ID NO: 2).

SEQ ID NO: 1: *S. aureus* gRNA component
[N]$_{16-24}$
GTTTTAGTACTCTGGAAA<u>CAGAATCTACTAAAACAAGGCAAAATGCC GTGTTTATCTCGTCAACTTGTTGGCGAGATTTTTT</u>

SEQ ID NO: 2: *S. aureus* gRNA component
[N]$_{16-24}$
GTTATAGTACTCTGGAAA<u>CAGAATCTACTATAACAAGGCAAAATGCC GTGTTTATCTCGTCAACTTGTTGGCGAGATTTTTT</u>

SEQ ID NO: 3: crRNA component
GTTTTAGTACTCTG

SED ID NO: 4: crRNA component
GTTATAGTACTCTG

SEQ ID NO: 5: tracrRNA component
CAGAATCTACTAAAACAAGGCAAAATGCCGTGTTTATCTCGTCAACTTG TTGGCGAGATTTTTT SEQ ID NO: 6: tracrRNA component
CAGAATCTACTATAACAAGGCAAAATGCCGTGTTTATCTCGTCAACTTG TTGGCGAGATTTTTT In some embodiments, the gRNA is an *S. pyogenes* gRNA comprising any one of the sequences set forth in SEQ ID NOs: 7-16 (which correspond to SEQ ID NOs: 2404, 2407, 2408, and 1-7 of WO 2014/144592)

SEQ ID NO: 7: S. pyogenes gRNA
(X$_{17-20}$) GUUUUAGAGCUA;

SEQ ID NO: 8: S. pyogenes gRNA
(X$_{17-20}$) GUUUUAGAGCUAUGCUGUUUUG

SEQ ID NO: 9: S. pyogenes gRNA
(X$_{17-20}$) GUUUUAGAGCUAUGCU

SEQ ID NO: 10: S. pyogenes gRNA
(X$_{17-20}$) GUUUUAGAGCUAGAAAUAGCAAGUUAAAAUAAGGCUAGUCCG SEQ ID NO: 11: S. pyogenes gRNA
(X$_{17-20}$)
GUUUUAGAGCUAUGCUGAAAAGCAUAGCAAGUUAAAAUAAGGCUAG
UCCGUUAUC SEQ ID NO: 12: S. pyogenes gRNA
(X$_{17-20}$)
GUUUUAGAGCUAUGCUGUUUUGGAAACAAAACAGCAUAGCAAGUUAA
AAUAAGGCUAGUCCGUUAUC SEQ ID NO: 13: S. pyogenes gRNA
(X$_{17-20}$)
GUUUUAGAGCUAGAAAUAGCAAGUUAAAAUAAGGCUAGUCCGUUAU
CAACUUGAAAAAGUGGCACCGAGUCGGUGC SEQ ID NO: 14: S. pyogenes gRNA
(X$_{17-20}$)
GUUUAAGAGCUAGAAAUAGCAAGUUUAAAUAAGGCUAGUCCGUUAUC
AACUUGAAAAAGUGGCACCGAGUCGGUGC SEQ ID NO: 15: S. pyogenes gRNA
(X$_{17-20}$)
GUUUUAGAGCUAUGCUGGAAACAGCAUAGCAAGUUUAAAUAAGGCUAG
UCCGUUAUCAACUUGAAAAAGUGGCACCGAGUCGGUGC SEQ ID NO: 16: S. pyogenes gRNA
(X$_{17-20}$)
GUUUAAGAGCUAUGCUGGAAACAGCAUAGCAAGUUUAAAUAAGGCUAG
UCCGUUAUCAACUUGAAAAAGUGGCACCGAGUCGGUGC wherein X$_{17-20}$ is a complementarily region that is complementary to 17-20 consecutive nucleotides of the complementary strand of a selected target sequence, preferably a target sequence immediately 5' a protospacer adjacent motif (PAM).

In some embodiments, the nucleic acids comprise a vector, e.g., a viral delivery vector. In some embodiments, the viral delivery vector comprises a promoter for Cas9, e.g., a CMV, EFS, or hGRK1 promoter. In some embodiments, the viral delivery vector comprises a promoter for the gRNA, e.g., a U6 promoter.

In some embodiments, the viral delivery vector comprises an adeno-associated virus (AAV) vector.

In some embodiments, the nucleic acids comprise (i) a first guide RNA (gRNA) comprising a sequence targeting a domain in intron 1 or 3 of the human RP1 gene, and a second gRNA comprising a sequence targeting a domain in intron 3 or exon 4 of the human RP1 gene, or a single guide RNA comprising a sequence selected from the group listed in Table 6; (ii) a first and a second inverted terminal repeat sequence (ITR); (iii) a promoter, e.g., a U6 promoter, for driving expression of the first and second gRNAs; and
(iv) a promoter for driving expression of the Cas9, preferably selected from the group consisting of a CMV, an EFS, or an hGRK1 promoter. In some embodiments, the promoter driving expression of a gRNA is an H1 or 7SK promoter.

Also provided are the nucleic acids described herein for use in therapy, as well as the nucleic acids described herein for use in preparation of a medicament, or for use in a method of treating a subject who has a condition associated with a mutation in RP1.

In some embodiments, the condition is autosomal dominant retinitis pigmentosa (adRP).

In some embodiments, the AAV vector is delivered to a retina of a subject by injection, such as by subretinal injection.

Also provided herein are methods for altering the genome of a cell. The methods comprise using CRISPR editing to form a first double strand break within intron 1 or 3 of the human RP1 gene and a second double strand within intron 3 or 4 of the human RP1 gene. In some embodiments, the cell is a cell of the eye of a mammal, e.g., human.

In some embodiments, the first and second double strand breaks are generated using a pair of gRNAs comprising sequences selected from Table 6.

In some embodiments, the first and second double strand breaks are repaired by non-homologous end joining (NHEJ) in a manner that results in removal of all or part of exon 2, exon 3, and exon 4 of a mutant allele of an RP1 gene on chromosome 8, sufficient to disrupt expression of the RP1 protein from that allele.

In some embodiments, the first and second double strand breaks are repaired by non-homologous end joining (NHEJ) in a manner that results in removal of (a) all of exon 2 and exon 3; (b) part of exon 4; or (c) all of exon 2 and exon 3 and part of exon 4; of a mutant allele of an RP1 gene on chromosome 8, sufficient to disrupt expression of the RP1 protein from that allele. In some embodiments, the first and second double strand breaks are repaired by non-homologous end joining (NHEJ) in a manner that results in removal of all or part of exon 2 and exon 3, or exon 4 of a mutant allele of an RP1 gene on chromosome 8, sufficient to disrupt expression of the RP1 protein from that allele.

In some embodiments, the first and/or second gRNA is configured to form a complex with a Cas9 molecule.

In some embodiments, the cell is from a subject suffering from autosomal dominant retinitis pigmentosa (adRP).

In some embodiments, the cell is a retinal cell or a photoreceptor cell.

In some embodiments, the photoreceptor cell is a cone photoreceptor cell or a cone cell, a rod photoreceptor cell or a rod cell or a macular cone photoreceptor cell.

Further, provided herein are methods for altering a cell. The methods include contacting the cell with a recombinant viral particle comprising a nucleotide sequence encoding a first gRNA comprising a sequence targeting a domain in intron 1 or 3 of the human RP1 gene, preferably as shown in Table 6; a nucleotide sequence encoding a second gRNA molecule comprising a sequence targeting a domain in intron 3 or exon 4 of the human RP1 gene, preferably as shown in Table 6; and a nucleotide sequence encoding a Cas9 molecule; wherein said viral particle is capable of delivery to a non-dividing cell, and wherein said contacting results in removal of all or part of exon 2, exon 3, and exon 4 of a mutant allele of an RP1 gene on chromosome 8, sufficient to disrupt expression of the RP1 protein from that allele.

In some embodiments, the methods include contacting the cell with a recombinant viral particle comprising a nucleotide sequence encoding a first gRNA comprising a sequence targeting a domain in intron 1 or 3 of the human RP1 gene, preferably as shown in Table 6; a nucleotide sequence encoding a second gRNA molecule and a second gRNA comprising a sequence targeting a domain in intron 3 or exon 4 of the human RP1 gene, preferably as shown in Table 6; and a nucleotide sequence encoding a Cas9 molecule; wherein said viral particle is capable of delivery to a non-dividing cell, and wherein said contacting results in removal of all or part of exon 2 and exon 3, or exon 4 of a mutant allele of an RP1 gene on chromosome 8, sufficient to disrupt expression of the RP1 protein from that allele.

In some embodiments, the viral particle is an adeno-associated virus (AAV) viral particle.

In some embodiments of the methods and nucleic acids described herein, the first gRNA and the second gRNA are shown in Table 6.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2A shows screening of individual sgRNAs for Haplotype 1 variants. FIG. 2B shows screening of individual sgRNAs for Haplotype 2 and 3 variants. Plasmids encoding individual sgRNAs were co-transfected with Cas9 expressing plasmids (SpCas9-WT and SpCas9-VRQR), into human cell lines carrying hetero- or homozygous RP1 haplotypes. Target spanning polymerase chain reaction (PCR) was performed, and amplicons were subjected to next-generation sequencing (NGS). Editing efficiency was calculated as the percentage of edited reads/total reads per allele.

FIG. 5A shows screening of RP1 expression in near-haploid (HAP-1) clonal cell-lines engineered with an EF1a promoter insertion. FIG. 5B shows RP1 expression level in engineered HAP-1 stable cell-lines relative to Weri-Rb1 cells. RP1 expression was quantified by qRT-PCR. Engineered HAP1-EF1a-RP1 Clone 5-1 has the highest expression of RP1 transcripts, with a four-fold increase over endogenous RP1 expression in Weri-Rb1 cells.

DETAILED DESCRIPTION

Figure 1:
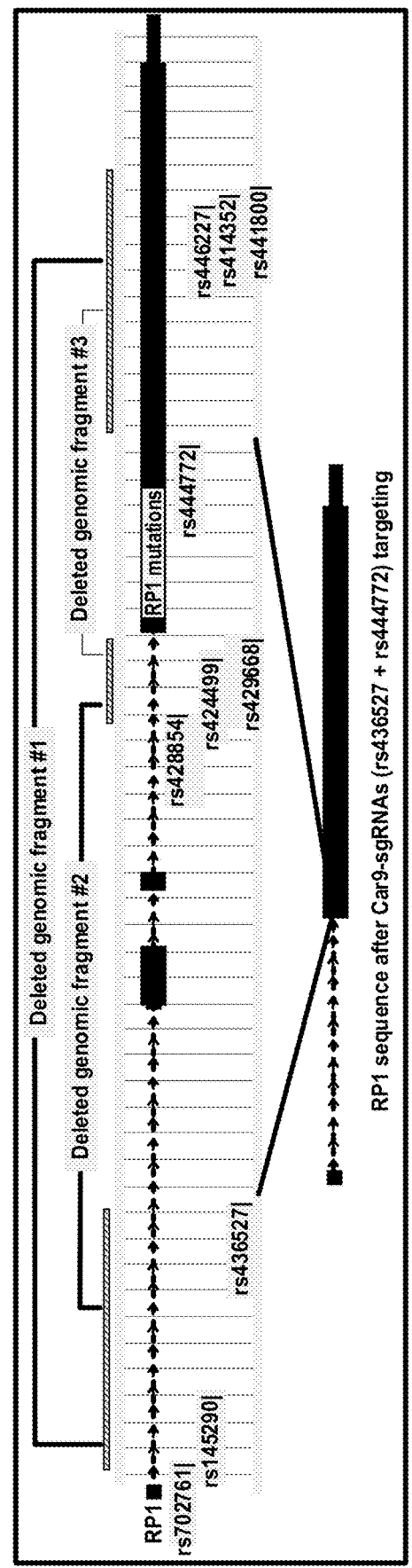
FIG. 1 shows common SNP-based CRISPR/Cas9 targeting strategy for mutant RP1 alleles. One of the RP1 haplotype has 3 common SNPs in intron 1, 3 SNPs in intron 3, and 4 SNPs in the last exon. Simultaneously targeting of one SNP in intron 1 or 3, and the other SNPs in intron 3 or exon 4, will delete the RP1 genomic regions (top), which will result in knockout of the RP1 allele. An example of combined target of SNP rs436527 in intron 1 and rs444772 in exon 4 is shown at the bottom.

The effects of dominant mutations can arise via gain-of-function, dominant-negative, or haploinsufficiency mechanisms. The primary challenge in developing a gene therapy for autosomal dominant RP (adRP) is that, in addition to delivery of a healthy gene, the mutant gene may also need to be suppressed (Lewin, A. S., et al., (1998). Nat. Med. 4(8): p. 967-971; O'Reilly, M., et al., (2008). Vision Research, 48(3): p. 386-91; and O'Reilly, M., et al., (2007) American Journal of Human Genetics, 81(1): p. 127-35). The second challenge is that, for many IRD genes, the therapeutic dosage falls within a narrow window such that overexpression of the normal gene can lead to retinal degeneration (O'Reilly, M., et al., (2008) Vision Research. 48(3): p. 386-91; Wen, X. H., et al., (2009) Biophys J, 96(3): p. 939-50; and Liu, Q., et al., (2012) PLoS One, 7(8): p. e43251). For example, in a transgenic Rp1 mouse line, a 50% excess of Rp1 over the physiological normal levels causes an RP-like retinal degeneration (Liu, Q., et al., (2012) PLoS One, 7(8): p. e43251). Therefore, an optimal therapeutic approach for dominant RP would require not only removal of the mutant protein, but also maintenance of endogenous levels of wild-type protein expression. CRISPR/Cas9 based genome editing tools provide a reliable and practical means to conceivably edit the disease-causing mutations in mammalian cells by introducing double strand breaks (DSBs) near the mutation, which are then repaired through the non-homologous end joining (NHEJ) or homology-directed repair (HDR) pathway, leading to the loss or correction of the mutant allele (Yin, H., et al., (2014) Nat Biotechnol, 2014. 32(6): p. 551-3; Ran, F. A., et al., (2015) Nature, 2015. 520(7546): p. 186-91; Swiech, L., et al., (2015) Nat Biotechnol, 2015. 33(1): p. 102-6; Tabebordbar, M., et al., (2016) Science, 2016. 351(6271): p. 407-11; Yang, Y., et al., (2016). Nature Biotechnology, 2016. 34(3): p. 334-8). By directly altering the genomic DNA, the CRISPR/Cas9 system is capable of maintaining the edited gene under its endogenous expression stoichiometry, thereby avoiding ectopic expression and abnormal gene production that may occur with conventional gene augmentation therapies. Recent studies of the RHO form of adRP demonstrated that the Cas9-sgRNA system is capable of distinguishing the single base pair difference between the wild-type and mutant P23H allele of the rhodopsin gene, and thus specifically disrupting the expression of mutant allele in mouse retina. This mutation-based gene knockout approach, however, requires developing an individual Cas9-sgRNA targeting system for each of the pathogenic mutations in a given gene, which limits its application for treating a larger number of patients.

Dominant mutations identified to date in RP1 are either nonsense or frameshift mutations that cluster at the N-terminal half of the last exon, exon 4 (Gandra, M., et al., (2008). Mol. Vis., 14: p. 1105-1113; Chen, L. J., et al., (2009). Invest Ophthalmol.Vis.Sci. 51(4): p. 2236-2242; Liu, Q., et al, (2009) Investigative ophthalmology & visual science 50(4): p. 1566-74; Liu, Q., et al., (2012). PLoS One, 7(8): p. e43251). The mutant RP1 alleles are predicted to encode truncated proteins that play a dominant negative role in photoreceptors (Liu, Q., et al., (2012). PLoS One, 7(8): p. e43251; Liu, Q., A. et al (2009), Invest Ophthalmol Vis Sci, 50(4): p. 1566-74; and Liu, Q., et al. (2004) J Neurosci, 24(29): p. 6427-36). The most common mutation in RP1, R677X, is present in approximately 3% of patients with adRP in the United States, making it the third most common adRP mutation (Jacobson, S. G., et al., (2000) *Investigative ophthalmology & visual science,* 41(7): p. 1898-908; Berson, E. L., et al., (2001) *Investigative ophthalmology & visual science,* 42(10): p. 2217-24; Schwartz, S. B., et al., (2003) *Investigative Ophthalmology & Visual Science,* 44(8): p. 3593-7; and Gamundi, M. J., et al., (2006) *BMC. Med.Genet.,* 7: p. 35). All dominant RP1 mutations are located in the last exon, and the resulting transcripts from such alleles escape nonsense-mediated decay to produce truncated proteins. Thus, disruption of the mutation by Cas9 cleavage and NHEJ repair will only create a new frameshift or truncating indel in the last exon, resulting in persistence of toxic gene products.

The present methods employ a paired-sgRNA targeting approach using common SNPs as surrogate targeting sites to disrupt the expression of mutant RP1 alleles (FIG. 1). This strategy could be applied to any autosomal dominant mutation in RP1, and would avoid the need for additional gene augmentation therapies, since the wild-type allele remains under its endogenous expression stoichiometry, and 50% of RP1 expression is sufficient for normal retinal integrity and function. The combined frequency of the three most common RP1 haplotypes is 93%, and the total homozygous frequency of the three common haplotypes is 35%. This indicates that approximately two thirds of the general population is heterozygous for RP1 haplotypes, which can be specifically targeted by the SNP-based CRISRP/Cas9 gene editing technology.

Thus, provided herein are methods and compositions for use in treating subjects who have dominant mutations in RP1.

RNA-Guided Nucleases (RGNs) and Guide RNAs

The present methods include the use of paired RNA-guided nucleases (RGNs) targeted to SNPs in a mutant allele of RP1, to excise portions of and disrupt the expression of the mutant RP1 alleles. The methods can include the use of RGNs including Cas9, Cpf1, and orthologs thereof.

The Cas9 nuclease from *S. pyogenes* can be guided via simple base pair complementarity between 17-20 nucleotides of an engineered guide RNA (gRNA), e.g., a single guide RNA or crispr RNA/trans-activated crispr RNA (crRNA/tracrRNA) pair, and the complementary strand of a target genomic DNA sequence of interest that lies next to a protospacer adjacent motif (PAM), e.g., a PAM matching the sequence NGG or NAG (Shen et al., (2013) *Cell Res*; Dicarlo et al., (2013) *Nucleic Acids Res*; Jiang et al., (2013) *Nat Biotechnol* 31, 233-239; Jinek et al., (2013) Elife 2, e00471; Hwang et al., (2013) *Nat Biotechnol* 31, 227-229; Cong et al., (2013) *Science* 339, 819-823; Mali et al., (2013) *Science* 339, 823-826; Cho et al., (2013) *Nat Biotechnol* 31, 230-232; Jinek et al., (2012) *Science* 337, 816-821). See, e.g., the sequences set forth in SEQ ID NOs: 7-16. The engineered CRISPR from *Prevotella* and *Francisella* 1 (Cpf1, also known as Cas12a) nuclease can also be used, e.g., as described in Zetsche et al., (2015) *Cell* 163, 759-771; Schunder et al., (2013) *Int J Med Microbiol* 303, 51-60; Makarova et al., (2015) *Nat Rev Microbiol* 13, 722-736; Fagerlund et al., (2015) *Genome Biol* 16, 251. Unlike SpCas9, Cpf1/Cas12a requires only a single 42-nt crRNA, which has 23 nt at its 3' end that are complementary to the protospacer of the target DNA sequence (Zetsche et al., (2015) *Cell* 163, 759-771). Furthermore, whereas SpCas9 recognizes an NGG PAM sequence that is 3' of the protospacer, AsCpf1 and LbCp1 recognize TTTN PAMs that are found 5' of the protospacer (Id.).

In some embodiments, the present system utilizes a wild type or variant Cas9 protein from *S. pyogenes* or *Staphylococcus aureus*, or a wild type or variant Cpf1 protein from *Acidaminococcus* sp. BV3L6 or Lachnospiraceae bacterium ND2006 either as encoded in bacteria or codon-optimized for expression in mammalian cells and/or modified in its PAM recognition specificity and/or its genome-wide specificity. A number of variants have been described; see, e.g., WO 2016/141224, PCT/US2016/049147, Kleinstiver et al., (2016) *Nat Biotechnol.* August; 34(8): 869-74; Tsai and Joung, (2016) *Nat Rev Genet.* May; 17(5): 300-12; Kleinstiver et al., (2016) *Nature.* January 28; 529(7587): 490-5; Shmakov et al., (2015) *Mol Cell.* November 5; 60(3): (2015) 385-97; Kleinstiver et al., *Nat Biotechnol.* December; 33(12): 1293-1298; Dahlman et al., (2015) *Nat Biotechnol.* November; 33(11): 1159-61; Kleinstiver et al., (2015) *Nature.* July 23; 523(7561): 481-5; Wyvekens et al., (2015) *Hum Gene Ther.* July; 26(7): 425-31; Hwang et al., (2015) *Methods Mol Biol.* 1311:317-34; Osborn et al., (2015) *Hum Gene Ther.* February; 26(2): 114-26; Konermann et al., (2015) *Nature.* January 29; 517(7536): 583-8; Fu et al., (2014) *Methods Enzymol.* 546:21-45; and Tsai et al., (2014) *Nat Biotechnol.* June; 32(6): 569-76, inter alia. Exemplary guide RNAs used with *S. aureus* include those set forth in SEQ ID NOs: 1-6.

Cas9 and analogs are shown in Table 1, and engineered protospacer-adjacent motif (PAM) or high-fidelity variants are shown in Table 2.

TABLE 1

List of Exemplary Cas9 or Cas12a Orthologs

| Ortholog | UniProt or GenBank Accession Number |
|---|---|
| *S. pyogenes* Cas9 (SpCas9) | Q99ZW2.1 |
| *S. aureus* Cas9 (SaCas9) | J7RUA5.1 |
| *S. thermophilus* Cas9 (St1Cas9) | G3ECR1.2 |
| *S. pasteurianus* Cas9 (SpaCas9) | BAK30384.1 |
| *C. jejuni* Cas9 (CjCas9) | Q0P897.1 |
| *F. novicida* Cas9 (FnCas9) | A0Q5Y3.1 |
| *P. lavamentivorans* Cas9 (PlCas9) | A7HP89.1 |
| *C. lari* Cas9 (ClCas9) | G1UFN3.1 |
| *Pasteurella multocida* Cas9 | Q9CLT2.1 |
| *F. novicida* Cpf1 (FnCpf1) | A0Q7Q2.1 |
| *M. bovoculi* Cpf1 (MbCpf1) | WP_052585281.1 |
| *A. sp.* BV3L6 Cpf1 (AsCpf1) | U2UMQ6.1 |
| *L. bacterium* N2006 (LbCpf1) | A0A182DWE3.1 |

TABLE 2

List of Exemplary High Fidelity and/or PAM-relaxed RGN Orthologs

| Published HF/PAM-RGN variants | PMID/US PGPUB | Mutations* |
|---|---|---|
| *S. pyogenes* Cas9 (SpCas9) eSpCas9 | 26628643 | K810A/K1003A/R1060A (1.0); K848A/K1003A/R1060A (1.1) |

TABLE 2-continued

List of Exemplary High Fidelity and/or PAM-relaxed RGN Orthologs

| Published HF/PAM-RGN variants | PMID/US PGPUB | Mutations* |
|---|---|---|
| *S. pyogenes* Cas9 (SpCas9) evoCas9 | 29431739 | M495V/Y515N/K526E/R661Q; (M495V/Y515N/K526E/R661S; M495V/Y515N/K526E/R661L) |
| *S. pyogenes* Cas9 (SpCas9) HF1 | 26735016 | N497A/R661A/Q695A/Q926A |
| *S. pyogenes* Cas9 (SpCas9) HiFi Cas9 | 30082871 | R691A |
| *S. pyogenes* Cas9 (SpCas9) HypaCas9 | 28931002 | N692A, M694A, Q695A, H698A |
| *S. pyogenes* Cas9 (SpCas9) Sniper-Cas9 | 30082838 | F539S, M763I, K890N |
| *S. pyogenes* Cas9 (SpCas9) xCas9 | 29512652 | A262T, R324L, S409I, E480K, E543D, M694I, E1219V |
| *S. pyogenes* Cas9 (SpCas9) SpCas9-NG | 30166441 | R1335V, L1111R, D1135V, G1218R, E1219F, A1322R, T1337R |
| *S. pyogenes* Cas9 (SpCas9) VQR/VRER | 26098369 | D1135V, R1335Q, T1337R; D1135V/G1218R/R1335E/T1337R |
| *S. aureus* Cas9 (SaCas9)-KKH | 26524662 | E782K/N968K/R1015H |
| enAsCas12a | US 20190010481 | One or more of: E174R, S170R, S542R, K548R, K548V, N551R, N552R, K607R, K607H, e.g., E174R/S542R/K548R, E174R/S542R/K607R, E174R/S542R/K548V/N552R, S170R/S542R/K548R, S170R/E174R, E174R/S542R, S170R/S542R, E174R/S542R/K548R/N551R, E174R/S542R/K607H, S170R/S542R/K607R, or S170R/S542R/K548V/N552R |
| enAsCas 12a-HF | US 20190010481 | One or more of: E174R, S542R, K548R, e.g., E174R/S542R/K548R, E174R/S542R/K607R, E174R/S542R/K548V/N552R, S170R/S542R/K548R, S170R/E174R, E174R/S542R, S170R/S542R, E174R/S542R/K548R/N551R, E174R/S542R/K607H, S170R/S542R/K607R, or S170R/S542R/K548V/N552R, with the addition of one or more of: N282A, T315A, N515A and K949A |
| enLbCas 12a(HF) | US 20190010481 | One or more of T152R, T152K, D156R, D156K, Q529K, G532R, G532K, G532Q, K538R, K538V, D541R, Y542R, M592A, K595R, K595H, K595S or K595Q, e.g., D156R/G532R/K538R, D156R/G532R/K595R, D156R/G532R/K538V/Y542R, T152R/G532R/K538R, T152R/D156R, D156R/G532R, T152R/G532R, D156R/G532R/K538R/D541R, D156R/G532R/K595H, T152R/G532R/K595R, T152R/G532R/K538V/Y542R, optionally with the addition of one or more of: N260A, N256A, K514A, D505A, K881A, S286A, K272A, K897A |
| enFnCas12a(HF) | US 20190010481 | One or more of T177A, K180R, K180K, E184R, E184K, T604K, N607R, N607K, N607Q, K613R, K613V, D616R, N617R, M668A, K671R, K671H, K671S, or K671Q, e.g., E184R/N607R/K613R, E184R/N607R/K671R, E184R/N607R/K613V/N617R, K180R/N607R/K613R, K180R/E184R, E184R/N607R, K180R/N607R, E184R/N607R/K613R/D616R, E184R/N607R/K671H, K180R/N607R/K671R, K180R/N607R/K613V/N617R, optionally with the addition of one or more of: N305A, N301A, K589A, N580A, K962A, S334A, K320A, K978A |

*predicted based on UniRule annotation on the UniProt database.

In some embodiments an RGN sequence is modified to include a nuclear localization sequences (NLSs), e.g., at the C- and/or N-terminus of the RGN protein, and a mini-polyadenylation signal (or Poly-A sequence). Exemplary NLSs include SV40 large T antigen NLS (PKKKRRV (SEQ ID NO: 17)); PKKKRKV (SEQ ID NO: 18); KRTADGSEF-ESPKKKRKV (SEQ ID NO: 19); and nucleoplasmin NLS (KRPAATKKAGQAKKKK (SEQ ID NO:20)). Other NLSs are known in the art; see, e.g., Cokol et al., (2000) *EMBO Rep.* November 15; 1(5): 411-415; Freitas and Cunha, (2009) *Curr Genomics*. December; 10(8): 550-557; and Leung et al (2003) *Journal of Biol Chem.* 278(43): 41947-41953. An exemplary polyadenylation signal is TAGCAATAAAGGATCGTTTATTTTCATTG-GAAGCGTGTG TTGGTTTTTTGATCAGGCGCG (SEQ ID NO: 21)).

Guide RNAs appropriate for the RGN should be used. In some embodiments, the gRNAs used in the present disclosure can be unimolecular or modular, as known in the art.

Vectors

Sequences encoding the RGN and guide RNA can be delivered to the retina, e.g., using a viral vector. Described herein are targeted expression vectors for in vivo transfection and expression of a polynucleotide that encodes a RGN and guide RNAs as described herein, in the retina, e.g., in photoreceptors, e.g., primarily or only in photoreceptors. Expression constructs of such components can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, alphavirus, vaccinia virus, or recombinant bacterial or eukaryotic plasmids; preferred viral vectors are adeno-associated virus type 2 (AAV2), AAV5 or AAV8. Viral vectors transfect cells directly; plasmid DNA can be delivered naked or with the help of, for example, cationic liposomes (lipofectamine) or derivatized (e.g., antibody conjugated), cationic dendrimers, inorganic vectors (e.g., iron oxide magnetofection), lipidoids, cell-penetrating peptides, cyclodextrin polymer (CDP), polylysine conjugates, gramacidin S, artificial viral envelopes or other such intracellular carriers, as well as direct injection of the gene construct or CaPO4 precipitation carried out in vivo.

An exemplary approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Viral vectors can be used as a recombinant gene delivery system for the transfer of exogenous genes in vivo, particularly into humans. These vectors provide efficient delivery of genes into cells, and in some cases the transferred nucleic acids are stably integrated into the chromosomal DNA of the host. Protocols for producing recombinant viruses and for infecting cells in vitro or in vivo with such viruses can be found in Ausubel, et al., eds., *Gene Therapy Protocols Volume 1: Production and In Vivo Applications of Gene Transfer Vectors*, Humana Press, (2008), pp. 1-32 and other standard laboratory manuals.

A preferred viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro and Immunol. 158:97-129 (1992); see also Domenger and Grimm, Human Molecular Genetics, 28(R1): R3-R14 (October 2019)). AAV vectors efficiently transduce various cell types and can produce long-term expression of transgenes in vivo. Although AAV vector genomes can persist within cells as episomes, vector integration has been observed (see for example Deyle and Russell, Curr Opin Mol Ther. 2009 August; 11(4): 442-447; Asokan et al., Mol Ther. 2012 April; 20(4): 699-708; Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989)). AAV vectors, particularly AAV2, have been extensively used for gene augmentation or replacement and have shown therapeutic efficacy in a range of animal models as well as in the clinic; see, e.g., Mingozzi and High, (2011) *Nature Reviews Genetics* 12, 341-355; Deyle and Russell, (2009) *Curr Opin Mol Ther.* August; 11(4): 442-447; Asokan et al., (2012) Mol Ther. April; 20(4): 699-708. AAV vectors containing as little as 300 base pairs of AAV can be packaged and can produce recombinant protein expression. Space for exogenous DNA is limited to about 4.5 kb. For example, an AAV1, 2, 4, 5, or 8 vector can be used to introduce DNA into the retina, e.g., into photoreceptors, inner retinal cells, or RPE cells (such as those described in Maguire et al. (2008). *N Engl J Med* 358: 2240-2248; Maguire et al. (2009). *Lancet* 374: 1597-1605; Bainbridge et al. (2008). *N Engl J Med* 358: 2231-2239; Hauswirth et al. (2008). *Hum Gene Ther* 19: 979-990; Cideciyan et al. (2008). *Proc Natl Acad Sci USA* 105: 15112-15117; Cideciyan et al. (2009). *N Engl J Med* 361: 725-727; Simonelli et al. (2010). *Mol Ther* 18: 643-650; Acland, et al. (2005). *Mol Ther* 12: 1072-1082; Le Meur et al. (2007). *Gene Ther* 14: 292-303; Stieger et al. (2008). *Mol Ther* 16: 916-923; and Vandenberghe et al. (2011). *Sci Transl Med* 3: 88ra54). In some embodiments, the AAV vector can include (or include a sequence encoding) an AAV capsid polypeptide described in WO 2015054653; for example, a virus particle comprising an AAV capsid polypeptide having an amino acid sequence selected from the group consisting of SEQ ID NOs: 1, 3, 5, 7, 9, 11, 13, 15, and 17 of WO 2015054653, and a RGN and guide RNA-encoding sequences as described herein. In some embodiments, the AAV capsid polypeptide is as shown in Table 1 of WO 2015054653, reproduced here:

| Node | Polypeptide (SEQ ID NO) | Nucleic Acid (SEQ ID NO) |
| --- | --- | --- |
| Anc80 | 1 | 2 |
| Anc81 | 3 | 4 |
| Anc82 | 5 | 6 |
| Anc83 | 7 | 8 |
| Anc84 | 9 | 10 |
| Anc94 | 11 | 12 |
| Anc113 | 13 | 14 |
| Anc126 | 15 | 16 |
| Anc127 | 17 | 18 |

In some embodiments, the AAV capsid polypeptide is an Anc80 polypeptide, e.g., an exemplary polypeptide shown in SEQ ID NO: 19 (Anc80L27); SEQ ID NO: 20 (Anc80L59); SEQ ID NO: 21 (Anc80L60); SEQ ID NO: 22 (Anc80L62); SEQ ID NO: 23 (Anc80L65); SEQ ID NO: 24 (Anc80L33); SEQ ID NO: 25 (Anc80L36); and SEQ ID NO: 26 (Anc80L44) of WO 2015054653.

A variety of nucleic acids have been introduced into different cell types using AAV vectors (see for example the references cited above and those cited in Asokan et al., (2012) *Molecular Therapy;* 20 4, 699-708; and Hermonat et al., (1984) *Proc. Nat. Acad. Sci. USA* 81:6466-6470; Tratschin et al., (1985) *Mol. Cell. Biol.* 4:2072-2081; Wondisford et al., (1988) *Mol. Endocrinol.* 2:32-39; Tratschin et al., (1984) *J. Virol.* 51:611-619; and Flotte et al., (1993) *J. Biol. Chem.* 268:3781-3790.

In some embodiments, a self-complementary AAV is used, which contains an inverted repeat genome that folds to make double-stranded DNA.

Retroviruses can also be used. The development of specialized cell lines (termed "packaging cells") which produce only replication-defective retroviruses has increased the utility of retroviruses for gene therapy, and defective retroviruses are characterized for use in gene transfer for gene therapy purposes (for a review see Katz et al., (2013) *Human Gene Therapy* 24:914). A replication defective retrovirus can be packaged into virions, which can be used to infect a target cell through the use of a helper virus by standard techniques. Examples of suitable retroviruses include pLJ, pZIP, pWE and pEM, which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest, but is inactivated in terms of its ability to replicate in a normal lytic viral life cycle. See, for example, Berkner et al., (1988) *BioTechniques* 6:616; Rosenfeld et al., (1991) *Science* 252:431-434; and Rosenfeld et al., (1992) *Cell* 68:143-155. Suitable adenoviral vectors derived from the adenovirus strain Ad type 5 d1324 or other strains of adenovirus (e.g., Ad2, Ad3, or Adz etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, (1986) *J. Virol.* 57:267.

In some embodiments, sequences encoding RGN and guide RNAs is entrapped in liposomes bearing positive charges on their surface (e.g., lipofectins), which can be tagged with antibodies against cell surface antigens of the target tissue (Mizuno et al., (1992) *No Shinkei Geka* 20:547-551; PCT publication WO91/06309; Japanese patent application 1047381; and European patent publication EP-A-43075).

The vectors can also include promoters, enhancers (e.g., CMV enhancer), other cis-regulatory elements, and/or capsid serotype variants. With regard to promoters, vectors can include promoters that drive expression in many cell types (e.g., cytomegalovirus (CMV), chicken β-actin (CBA), cytomegalovirus (CMV) enhancer fused to the chicken beta-actin promoter (CAG), CBh, elongation factor alpha 1 (EFalpha1), EF-1 Alpha Short (EFS) or CASI) or specifically in photoreceptor cells (e.g., RHO, beta phosphodiesterase (PDE), retinitis pigmentosa (RP1), rhodopsin kinase (hGRK1) and cone arrestin (CAR)) (see, e.g., Gray et al., (2011) *Hum Gene Ther*. September; 22(9): 1143-53; Alexopoulou et al., (2008) *BMC Cell Biol.;* 9: 2; Esumi et al., (2004) *Journal Biological Chemistry;* 279:19064-73; Guziewicz et al., (2013) *PLoS One.;* 8:e75666; Allocca et al., (2007) *J Virol;* 81:11372-80; see also Domenger and Grimm, (2019) Human Molecular Genetics, 28(R1):R3-R14 (October)). Other cis-regulatory elements can include enhancer elements derived from the interphotoreceptor retinoid-binding protein gene (IRBP), woodchuck hepatitis virus post-transcriptional regulatory element (WPRE), or minute virus of mice (MVM) intron (see Domenger and Grimm, (2019) *Human Molecular Genetics,* 28(R1):R3-R14 (October)).

The pharmaceutical preparation of the gene therapy construct can consist essentially of the gene delivery system (viral vector and any associated agents such as helper viruses, proteins, lipids, and so on) in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Alternatively, the methods can include delivering the RGN and guide RNA together, e.g., as a complex. For example, the RGN and gRNA can be can be overexpressed in a host cell and purified, then complexed with the guide RNA (e.g., in a test tube) to form a ribonucleoprotein (RNP), and delivered to cells. In some embodiments, the RGN can be expressed in and purified from bacteria through the use of bacterial expression plasmids. For example, His-tagged deaminase fusion protein can be expressed in bacterial cells and then purified using nickel affinity chromatography. The use of RNPs circumvents the necessity of delivering plasmid DNAs encoding the nuclease or the guide, or encoding the nuclease as an mRNA. RNP delivery may also improve specificity, presumably because the half-life of the RNP is shorter and there is no persistent expression of the nuclease and guide (in contrast to the sustained expression from a plasmid). The RNPs can be delivered to the cells in vivo or in vitro, e.g., using lipid-mediated transfection or electroporation. See, e.g., Liang et al. (2015) *Journal of biotechnol-* ogy 208: 44-53; Zuris, John A., et al. (2015) *Nature biotechnology* 33.1: 73-80; Kim et al. (2014) Genome research 24.6: 1012-1019.

Methods of Treatment

Provided herein are methods of treating subjects (e.g., mammalian subjects, e.g., human or non-human veterinary subjects) who have Retinitis pigmentosa (RP) associated with dominant mutations in the RP1 gene. Suitable subjects can be identified by one of skill in the art and a diagnosis confirmed by genetic testing (e.g., sequencing to identify the presence of a mutation in the subject's RP1 gene). A reference sequence for RP1 can be found in NCBI GenBank at RefSeqGene ID NG_009840.2 (Range 5030-19768).

The methods include administering an effective amount of an RGN and paired guide RNAs that excise portions of and disrupt the expression of the mutant RP1 alleles. In clinical settings, the vectors can be introduced into a subject by any of a number of methods, each of which familiar in the art. Although other methods can be used, in some embodiments, the route of choice for delivery of gene therapy vectors to the retina is via sub-retinal injection. This provides access to the RPE and photoreceptor cells of the retina. Different serotypes of AAV have been shown to transduce these cell populations effectively after sub-retinal injection in animal studies (Vandenberghe et al., (2013) *PLoS One.* 8:e53463. PMCID: 3559681; Vandenberghe and Auricchio, (2012) *Gene Therapy.* 19:162-8; Vandenberghe et al., (2011) *Science translational medicine.* 3:88ra54; Dinculescu et al., (2005) *HumGene Ther.* 16:649-63; Boye et al., (2013)*Mol Ther.* 21:509-19; and Alexander and Hauswirth, (2008) *Adv Exp Med Biol.* 2008; 613:121-8). The sub-retinal injection approach is being used in the ongoing clinical trials of gene augmentation therapy for retinal degeneration caused by mutations in the RPE65 and CHM genes (Maguire et al., (2008) *New England Journal of Medicine.* 358:2240-8; Bainbridge et al., (2008) *New England Journal of Medicine.* 358:2231-9; Cideciyan et al., (2008) *Proceedings National Academy Sciences USA.* 105:15112-7; Maguire et al., (2009) *Lancet.* 374:1597-605; Jacobson et al., (2012) *Archives Ophthalmology.* 130:9-24; Bennett et al., (2012) *Science translational medicine.* 4:120ra15; and MacLaren et al., (2014) *Lancet.* 383:1129-37). Sub-retinal injections can be performed using a standard surgical approach (e.g., as described in Maguire et al., 2008 supra; Bainbridge et al., 2008 supra; Cideciyan et al., 2008 supra; MacLaren et al., 2014 supra). See also WO2019/183641.

Any region of the retina may be targeted, though the fovea (which extends approximately 1 degree out from the center of the eye) may be preferred in certain instances due to its role in central visual acuity and the relatively high concentration of cone photoreceptors there relative to peripheral regions of the retina. Alternatively or additionally, injections may be targeted to parafoveal regions (extending between approximately 2 and 10 degrees off center), which are characterized by the presence of all three types of retinal photoreceptor cells. In addition, injections into the parafoveal region may be made at comparatively acute angles using needle paths that cross the midline of the retina. For instance, injection paths may extend from the nasal aspect of the sclera near the limbus through the vitreal chamber and into the parafoveal retina on the temporal side, from the temporal aspect of the sclera to the parafoveal retina on the nasal side, from a portion of the sclera located superior to the cornea to an inferior parafoveal position, and/or from an inferior portion of the sclera to a superior parafoveal position. The use of relatively small angles of injection relative to the retinal surface may advantageously reduce or limit the potential for spillover of vector from the bleb into the vitreous body and, consequently, reduce the loss of the vector during delivery. In other cases, the macula (inclusive of the fovea) can be targeted, and in other cases, additional retinal regions can be targeted, or can receive spillover doses.

Compositions comprising AAV vectors can be administered to subjects by any suitable means, including without limitation injection, for example, sub-retinal injection. The concentration of AAV vector within the composition is selected to ensure, among other things, that a sufficient AAV dose is administered to the retina of the subject, taking account of dead volume within the injection apparatus and the relatively limited volume that can be safely administered. Suitable doses may include, for example, $1\times10^{11}$ viral genomes (vg)/mL, $2\times10^{11}$ viral genomes (vg)/mL, $3\times10^{11}$ viral genomes (vg)/mL, $4\times10^{11}$ viral genomes (vg)/mL, $5\times10^{11}$ viral genomes (vg)/mL, $6\times10^{11}$ viral genomes (vg)/mL, $7\times10^{11}$ viral genomes (vg)/mL, $8\times10^{11}$ viral genomes (vg)/mL, $9\times10^{11}$ viral genomes (vg)/mL, $1\times10^{12}$ vg/mL, $2\times10^{12}$ viral genomes (vg)/mL, $3\times10^{12}$ viral genomes (vg)/mL, $4\times10^{12}$ viral genomes (vg)/mL, $5\times10^{12}$ viral genomes (vg)/mL, $6\times10^{12}$ viral genomes (vg)/mL, $7\times10^{12}$ viral genomes (vg)/mL, $8\times10^{12}$ viral genomes (vg)/mL, $9\times10^{12}$ viral genomes (vg)/mL, $1\times10^{13}$ vg/mL, $2\times10^{13}$ viral genomes (vg)/mL, $3\times10^{13}$ viral genomes (vg)/mL, $4\times10^{13}$ viral genomes (vg)/mL, $5\times10^{13}$ viral genomes (vg)/mL, $6\times10^{13}$ viral genomes (vg)/mL, $7\times10^{13}$ viral genomes (vg)/mL, $8\times10^{13}$ viral genomes (vg)/mL, or $9\times10^{13}$ viral genomes (vg)/mL. Any suitable volume of the composition may be delivered to the subretinal or cochlear space. In some instances, the volume is selected to form a bleb in the subretinal space, for example 1 microliter, 10 microliters, 50 microliters, 100 microliters, 150 microliters, 200 microliters, 250 microliters, 300 microliters, etc.

Further provided herein are viruses comprising sequences encoding an RGN and guide RNAs as described herein (e.g., one or more viruses comprising sequences one, two, or all three of the RGN and paired gRNAs, e.g., wherein a single virus comprises sequences encodes one, two (e.g., two gRNAs), or all three, as well as compositions comprising one or more of such viruses (e.g., a composition comprising one virus comprising sequences encoding the two gRNAs and a separate virus comprising a sequence encoding the RGN; a composition comprising one virus comprising sequences encoding the two gRNAs and the RGN; or a composition comprising one virus comprising a sequence encoding a first gRNA, a second virus comprising a sequence encoding a second gRNA, and a third virus comprising a sequence encoding the RGN). Also provided are RNPs comprising the RGN and gRNAs, and compositions comprising RNPs comprising the RGN and each of the gRNAs.

Examples

The invention is further described in the following examples, which do not limit the scope of the invention described in the claims.

SNP-Based CRISPR/Cas9 Gene-Editing System for RP1 Mutations

The three most common RP1 haplotypes (H1, H2 and H3, identified from the 1000 Genomes Phase1 variants for protein coding regions) occur with a frequency of 42.5%, 27% and 23.5%, respectively (Table 3). H1 is the reference sequence. Common SNPs on H2 include G at rs702761, G at rs145290, A at rs436527, A at rs428854, C at rs424499, C at rs429668, A at rs444772, A at rs446227, C at rs414352, and G at rs441800. Common SNPs on H3 include A for rs62514616, T for rs2293869, and A for rs61739567. The combined frequency of these three common haplotypes is 93% and the total homozygous frequency of the three common haplotypes is 35%. This indicates that approximately two thirds of the general population is heterozygous for RP1 haplotypes, which can be specifically targeted by the SNP-based CRISPR/Cas9 gene editing technology.

found that three SNPs (rs702761, rs145290 and rs436527) in intron 1 and three SNPs (rs428854, rs424499 and rs429668) in intron 3 had extremely tight linkage (D'=0.99 or 1) with the 4 common SNPs on H2 (Table 4). Several SNPs in the regulatory region are also tightly linked to H2. One SNP rs62514616 is tightly linked with the two common SNPs on H 3. These SNPs are all potential surrogates for our CRISPR/Cas9 editing approach that is described below.

TABLE 3

RP1 haplotypes from 1000 Genome Project

| Haplotypes | Haplotype Freq % | Homozygous Freq % | 1 rs702761 | 2 rs145290 | 3 rs436527 | 4 rs428854 | 5 rs424499 | 6 rs429668 | 7 rs444772 | 8 rs446227 | 9 rs414352 |
|---|---|---|---|---|---|---|---|---|---|---|---|
| H1 (Ref) | 42.5 | 19.1 | A | A | G | G | T | T | G | G | T |
| H2 | 27 | 8.42 | G | G | A | A | C | C | A | A | C |
| H3 | 23.5 | 7.51 | A | A | G | G | T | T | G | G | T |

| Haplo-types | Haplotype Freq % | Homo-zygous Freq % | 10 rs441800 | 11 rs62514616 | 12 rs2293869 | 13 rs61739567 |
|---|---|---|---|---|---|---|
| H1 (Ref) | 42.5 | 19.1 | A | G | A | G |
| H2 | 27 | 8.42 | G | G | A | G |
| H3 | 23.5 | 7.51 | A | A | T | A |

The allele frequencies for the four common SNPs (rs444772, rs446227, rs414352 and rs441800) on H2 is 0.25-0.27 in European Americans based on the 1000 Genomes Project (Table 4). The two SNPs (rs2293869 and

TABLE 4

SNPs that are in tight linkage on RP1 haplotype 1 and 2

| SNPs | Distance to R677* | Location | Ref | Alt | AF (EUR) | rs702761 | rs145290 | rs436527 | rs428854 | rs424499 | rs429668 | rs444772 |
|---|---|---|---|---|---|---|---|---|---|---|---|---|
| rs702761 | −9518 | Intron 1 | A | G | 0.27 | 1 | 1 | 1 | 1 | 1 | 1 | 1 |
| rs145290 | −8859 | Intron 1 | A | G | 0.26 | 1 | 1 | 1 | 1 | 1 | 1 | 1 |
| rs436527 | −6954 | Intron 1 | G | A | 0.25 | 1 | 1 | 1 | 1 | 0.99 | 0.99 | 0.99 |
| rs428854 | −2101 | Intron 3 | G | A | 0.25 | 1 | 1 | 1 | 1 | 0.99 | 0.99 | 0.99 |
| rs424499 | −1552 | Intron 3 | T | C | 0.26 | 1 | 1 | 0.99 | 0.99 | 1 | 1 | 1 |
| rs429668 | −1333 | Intron 3 | T | C | 0.26 | 1 | 1 | 0.99 | 0.99 | 1 | 1 | 1 |
| rs444772 | 586 | exon 4 | G | A | 0.26 | 1 | 1 | 0.99 | 0.99 | 1 | 1 | 1 |
| rs446227 | 2979 | exon 4 | G | A | 0.25 | 1 | 1 | 1 | 1 | 1 | 1 | 1 |
| rs414352 | 3042 | exon 4 | T | C | 0.26 | 1 | 1 | 0.99 | 0.99 | 1 | 1 | 1 |
| rs441800 | 3146 | exon 4 | A | G | 0.25 | 1 | 1 | 1 | 1 | 1 | 1 | 1 |

| SNPs | Distance to R677* | Location | Ref | Alt | AF (EUR) | rs446227 | rs414352 | rs441800 |
|---|---|---|---|---|---|---|---|---|
| rs702761 | −9518 | Intron 1 | A | G | 0.27 | 1 | 1 | 1 |
| rs145290 | −8859 | Intron 1 | A | G | 0.26 | 1 | 1 | 1 |
| rs436527 | −6954 | Intron 1 | G | A | 0.25 | 1 | 0.99 | 1 |
| rs428854 | −2101 | Intron 3 | G | A | 0.25 | 1 | 0.99 | 1 |
| rs424499 | −1552 | Intron 3 | T | C | 0.26 | 1 | 1 | 1 |
| rs429668 | −1333 | Intron 3 | T | C | 0.26 | 1 | 1 | 1 |
| rs444772 | 586 | exon 4 | G | A | 0.26 | 1 | 1 | 1 |
| rs446227 | 2979 | exon 4 | G | A | 0.25 | 1 | 1 | 1 |
| rs414352 | 3042 | exon 4 | T | C | 0.26 | 1 | 1 | 1 |
| rs441800 | 3146 | exon 4 | A | G | 0.25 | 1 | 1 | 1 |

*The distances shown are all relative to the most common R677X mutation in RP1 gene. D' is shown for each pair of SNPs.

rs61739567) for H3 have an allele frequency of 0.44 in European Americans. To reveal the common SNPs in non-coding regions for H2 and H3, we performed a linkage disequilibrium (LD) analysis using HaploReg v4.1. We From the IRD Biobank at MEEI, we collected 50 affected individuals from 38 families with dominant mutations in the RP1 gene. The most common mutation R677X was detected in 15 patients from 13 families. To determine the phase of the mutation with the SNPs of a given RP1 haplotype, we first analyzed the diploid genotype of RP1 using the NGS-based Genetic Eye Disease (GEDi) test results available from 20 RP1 patients. As shown in Table 5, 14 out of 20 patients are heterozygous at the RP1 locus, and 6 are homozygous for one of the three common haplotypes. The 19 unique dominant mutations that we found in our 38 RP1 families are all clustered in a small region at the beginning of exon 4 (c. 1199, p. Q400-c.2287, p. N763). We inspected the paired-end 2×150 bp NGS reads and identified that the 4 bp deletion mutation (c.2280_2284del) in sample 004-235 is in trans with rs444772 on Hap2, indicating that the mutation is on the same allele with Hap3 alleles. Thus, sgRNAs designed to target the SNPs on the Hap3 will be able to abolish the mutant allele in sample 004-235. However, the short NGS reads in the GEDi test could not determine the phase of other mutations with rs444772 due to the distance.

TABLE 5

RP1 haplotypes in adRP patients

| Sample ID | RP1 Mutation | Protein | Haplotypes | Diploid | rs444772 | rs2293869 | rs446227 | rs414352 | rs441800 | rs61739567 |
|---|---|---|---|---|---|---|---|---|---|---|
| OGI1188_002303 | c.1199_1200del | p.Q400NA | H2/H3 | het | het | het | het | het | het | het |
| OGI785_001529 | c.1468G > T | p.E490* | H3/H3 | hom | — | hom | — | — | — | hom |
| D00760_000782 | c.1555C > T | p.Q519* | H1/H3 | het | — | het | — | — | — | het |
| OGI712_001422 | c.1621_1621del | p.K541NA | H2/H2 | hom | hom | — | hom | hom | hom | — |
| D00827_000892 | c.1625C > G | p.S542* | H1/H1 | hom | — | — | — | — | — | — |
| JB431 | c.2029C > T | p.R677* | H2/H3 | het | het | het | het | het | het | het |
| JB44 | c.2029C > T | p.R677* | H2/H3 | het | het | het | het | het | het | het |
| OGI680_001363 | c.2029C > T | p.R677* | H2/H2 | het | het | — | het | het | het | — |
| D00827_000892 | c.2039_2040insA | p.A680NA | H1/H1 | hom | — | — | — | — | — | — |
| D01581_002136 | c.2039_2040insA | p.A680NA | H1/H1 | hom | — | — | — | — | — | — |
| OGI741_001462 | c.2056C > T | p.Q686* | H3/H3 | hom | — | hom | — | — | — | hom |
| D00520_000364 | c.2103_2106del | p.R701NA | H1/H3 | het | — | het | — | — | — | het |
| D227_1 | c.2103_2106del | p.R701NA | H1/H3 | het | — | het | — | — | — | het |
| 001-106 | c.2143C > T | p.Q715* | H2/H3 | het | het | het | het | het | het | het |
| FB000016 | c.2167G > T | p.G723* | H2/H3 | het | het | het | het | het | het | het |
| D01692_002340 | c.2219C > G | p.S740* | H1/H3 | het | — | het | — | — | — | het |
| OGI-327-776 | c.2219C > G | p.S740* | H1/H2 | het | het | — | het | het | het | — |
| OGI1153_002251 | c.2271_2271del | p.F757NA | H2/H3 | het | het | het | het | het | het | het |
| 004-235 | c.2280_2284del | p.N760NA | H2/H3 | het | het | het | het | het | het | het |
| D01627_002212 | c.2296C > T | p.Q766* | H1/H2 | het | het | — | het | het | het | — |

Design of Cas9-sgRNAs for Targeting SNPs on RP1 Haplotypes

For each of the SNPs, we searched available PAM motifs for wild-type SpCas9 (NGG), an engineered VRQR variant of SpCas9 (NGAN), wild-type *Staphylococcus aureus* Cas9 (SaCas9-WT, NNGRRT), and an engineered KKH variant of SaCas9 (NNNRRT). We designed 1-7 sgRNAs to target each SNP site within 13 bp proximal to the PAM or falling in the PAM (bolded) on the reference haplotype (Table 6). For guides targeted to H2 and H3, we switched the reference nucleotide (shown in bold) to the SNP nucleotide. Four gRNAs targeting the wild type genome in intron 3 were also designed.

TABLE 6

Cas9-sgRNAs for targeting SNPs on human RP1 haplotypes

| Site | SNPs | Seq | Cas9 | sgRNA ID | Protospacers | # | PAM | Targeted haplotypes |
|---|---|---|---|---|---|---|---|---|
| 1 | rs702761 | A/G | Sp-WT | 1A1 and 1G1 | ATGCTGATATTGAAR TAGAA | 22 | TGG | H1 or H3/H2 |
| | | | Sp-WT | 1A2 and 1G2 | TGCTGATATTG AARTAGAAT | 23 | GGAA | H1 or H3/H2 |
| | | | Sp-VRQR | 1A3 and 1G3 | CAATATGCTGAT ATTGAART | 24 | AGAA | H1 or H3/H2 |
| | | | Sa-WT | 1A4 and 1G4 | TCACAATATGCT GATATTGAAR | 25 | TAGAAT | H1 or H3/H2 |
| | | | Sa-KKH | 1A5 and 1G5 | TGATATTGAARTAG AATGGAAC | 26 | TTCAGT | H1 or H3/H2 |
| | | | Sa-KKH | 1A6 and 1G6 | TGATACTGAAGTT CCATTCTAY | 27 | TTCAAT | H1 or H3/H2 |
| 2 | rs145290 | A/G | Sp-VRQR | 2G1 | CATTGTCTAACTTTA GGCAA | 28 | TGAA | H2 |
| | | | Sp-VRQR | 2A2 and 2G2 | TGTCTAACTTTAGGC AATRA | 29 | AGAG | H1 or H3/H2 |

TABLE 6-continued

Cas9-sgRNAs for targeting SNPs on human RP1 haplotypes

| Site | SNPs | Seq | Cas9 | sgRNA ID | Protospacers | # | PAM | Targeted haplotypes |
|---|---|---|---|---|---|---|---|---|
| | | | Sp-VRQR | 2A3 and 2G3 | AGGCAATRAAGAGTCTCTGC | 30 | AGAN | H1 or H3/H2 |
| | | | Sa-WT | 2A4 and 2G4 | CATTGTCTAACTTTAGGCAATR | 31 | AAGAGT | H1 or H3/H2 |
| | | | Sa-KKH | 2A5 and 2G5 | TCTGCAGAGACTCTTYATTGCC | 32 | TAAAGT | H1 or H3/H2 |
| 3 | rs436527 | G/A | Sp-WT | 3R1 | ACGTGTGAGCCACCACGCCC | 33 | GGG | H1, H2, H3 |
| | | | Sp-WT | 3G2 | CACGTGTGAGCCACCACGCC | 34 | CGG | H1 |
| | | | Sp-WT | 3G3 and 3A3 | TTAAATAAGACTTTAGGCCY | 35 | GGG | H1 or H3/H2 |
| | | | Sp-WT | 3G4 and 3A4 | TAAGACTTTAGGCCYGGGCG | 36 | TGG | H1 or H3/H2 |
| | | | Sp-WT | 3G5 and 3A5 | GACTTTAGGCCYGGGCGTGG | 37 | TGG | H1 or H3/H2 |
| | | | Sa-KKH | 3G6 and 3A6 | TGTGAGCCACCACGCCCRGGCC | 38 | TAAAGT | H1 or H3/H2 |
| | | | Sa-KKH | 3G7 and 3A7 | TAAATAAGACTTTAGGCCYGGG | 39 | CGTGGT | H1 or H3/H2 |
| 4 | rs428854 | G/A | Sp-WT | 4G1 and 4A1 | TTTCTGCTTTCATAAARCTA | 40 | TGG | H1 or H3/H2 |
| | | | Sp-VRQR | 4G2 and 4A2 | TTCTGCTTTCATAAARCTAT | 41 | GGAN | H1 or H3/H2 |
| | | | Sp-VRQR | 4G3 and 4A3 | ATCCATAGYTTTATGAAAGC | 42 | AGAN | H1 or H3/H2 |
| | | | Sp-VRQR | 4G4 and 4A4 | AACAGGTATCCATAGYTTTA | 43 | TGAA | H1 or H3/H2 |
| | | | Sa-WT | 4G5 and 4A5 | ATGTTTCTGCTTTCATAAARCT | 44 | ATGGAT | H1 or H3/H2 |
| | | | Sa-KKH | 4A6 | TACACATATCAAAACAGGTATC | 45 | CATACT | H2 |
| 5 | rs424499 | T/C | Sp-WT | 5T1 and 5C1 | CAGGAGAATYGCTTGAACCC | 46 | TGG | H1 or H3/H2 |
| | | | Sp-WT | 5T2 and 5C2 | GAGAATYGCTTGAACCCTGG | 47 | AGG | H1 or H3/H2 |
| | | | Sp-VRQR | 5T3 and 5C3 | GCTGAAGCAGGAGAATYGCT | 48 | TGAA | H1 or H3/H2 |
| | | | Sp-VRQR | 5T4 and 5C4 | AGGAGAATYGCTTGAACCCT | 49 | GGAG | H1 or H3/H2 |
| | | | Sp-VRQR | 5C5 | CTCCACCTCCAGGGTTCAAG | 50 | CGAT | H2 |
| 6 | rs429668 | T/C | Sp-VRQR | 6C1 | TCCAAAGGAAGAGGCAGCAA | 51 | AGAA | H2 |
| 7 | rs444772 | G/A | Sp-WT | 7g1 and 7A1 | AAAACCAGAAAAAACRTAA | 52 | AGG | H1 or H3/H2 |
| | | | Sp-WT | 7G2 and 7A2 | AAAGCCAGAAAAAACRTAAA | 53 | GGG | H1 or H3/H2 |
| | | | Sp-WT | 7G3 and 7A3 | TATCCCCTTTAYGTTTTTTC | 54 | TGG | H1 or H3/H2 |
| | | | Sp-WT | 7G4 and 7A4 | AAGCCAGAAAAAACRTAAAG | 55 | GGG | H1 or H3/H2 |
| | | | Sp-VRQR | 7G5 and 7A5 | AGCCAGAAAAAACRTAAAGG | 56 | GGAT | H1 or H3/H2 |
| | | | Sa-WT | 7G6 and 7A6 | AAAAAGCCAGAAAAAACRTAAA | 57 | GGGGAT | H1 or H3/H2 |
| | | | Sa-KKH | 7G7 and 7A7 | GCCAGAAAAAACRTAAAGGGGA | 58 | TAAGT | H1 or H3/H2 |
| 8 | rs446227 | G/A | Sp-WT | 8G1 and 8A1 | ATCATAAAGACTTGYTTTCC | 59 | TGG | H1 or H3/H2 |
| | | | Sp-VRQR | 8G2 and 8A2 | TCCAGGAAARCAAGTCTTTA | 60 | TGAT | H1 or H3/H2 |
| | | | Sa-KKH | 8G3 and 8A3 | GTGTTCCAGGAAARCAAGTCTT | 61 | TATGAT | H1 or H3/H2 |
| 9 | rs414352 | T/C | Sp-WT | 9T1 and 9C1 | TAGTAGTTCAYCTATGTTGC | 62 | AGG | H1 or H3/H2 |
| | | | Sp-VRQR | 9T2 and 9C2 | AGTAGTTCAYCTATGTTGCA | 63 | GGAA | H1 or H3/H2 |
| | | | Sp-VRQR | 9T3 and 9C3 | TGGAATTCCTGCAACATAGR | 64 | TGAA | H1 or H3/H2 |
| | | | Sp-VRQR | 9T4 and 9C4 | TGCAACATAGRTGAACTACT | 65 | AGAT | H1 or H3/H2 |
| | | | Sa-KKH | 9T5 and 9C5 | TTCCTGCAACATAGRTGAACTA | 66 | CTAGAT | H1 or H3/H2 |

TABLE 6-continued

Cas9-sgRNAs for targeting SNPs on human RP1 haplotypes

| Site | SNPs | Seq | Cas9 | sgRNA ID | Protospacers | # | PAM | Targeted haplotypes |
|---|---|---|---|---|---|---|---|---|
|  |  |  | Sa-WT | 9T6 and 9C6 | TCTAGTAGTTC AYCTATGTTGC | 67 | AGGAAT | H1 or H3/H2 |
| 10 | rs441800 | A/G | Sp-VRQR | 10A1 and 10G1 | GAACCTGGTA CAAAACARAA | 68 | TGAT | H1 or H3/H2 |
|  |  |  | Sp-VRQR | 10A2 and 10G2 | CCTGGTACAA AACARAATGA | 69 | TGAT | H1 or H3/H2 |
|  |  |  | Sa-WT | 10G3 | CATTGTAGAAC CTGGTACAAAA | 70 | CAGAAT | H1 or H3/H2 |
|  |  |  | Sa-KKH | 10A4 and 10G4 | TGTAGAACCTG GTACAAAACAR | 71 | AATGAT | H1 or H3/H2 |
|  |  |  | Sa-KKH | 10A5 and 10G5 | AGAACCTGGTA CAAAACARAAT | 72 | GATGAT | H1 or H3/H2 |
|  |  |  | Sa-KKH | 10A6 and 10G6 | GCTATCATCAT TYTGTTTTGTA | 73 | CCAGGT | H1 or H3/H2 |
|  |  |  | Sa-WT | 10A7 and 10G7 | GTACAAAACAR AATGATGATAG | 74 | CAGAAT | H1 or H3/H2 |
| 11 | rs62514616 | G/A | Sp-WT | 11G1 and 11A1 | TCCCGAATAGC TGGGAYTAC | 75 | AGG | H1/H3 |
|  |  |  | Sp-WT | 11G2 and 11A2 | GGCCTGTART CCCAGCTATT | 76 | CGG | H1/H3 |
|  |  |  | Sp-WT | 11G3 and 11A3 | GCCTGTARTCC CAGCTATTC | 77 | GGG | H1/H3 |
|  |  |  | Sa-WT | 11A4 | CTGCTTCAGCA TCCCGAATAGC | 78 | TGGGAT | H1/H3 |
| 12 | rs2293869 | A/T | Sp-WT | 12A1 and 12T1 | TAGATWATCT CCTGTCAAAC | 79 | CGG | H1/H3 |
|  |  |  | Sp-WT | 12A2 and 12T2 | AGGAGATWAT CTATGTAAAG | 80 | AGG | H1/H3 |
|  |  |  | Sp-VRQR | 12A3 and 12T3 | ACAGGAGATW ATCTATGTAA | 81 | AGAG | H1/H3 |
|  |  |  | Sa-KKH | 12A4 | GACTTATCTCC CTCTTTACATA | 82 | GATAAT | H1 |
| 13 | rs61739567 | G/A | Sp-VRQR | 13G1 and 13A1 | TTTGAAGGAA AGGTTTTRTA | 83 | TGAA | H1/H3 |
|  |  |  | Sa-WT | 13G2 and 13A2 | AGATTTGAAGG AAAGGTTTTR | 84 | ATGAAT | H1/H3 |
| 14 | * |  | Sp-WT | 14N1 | TTTGAAGGAA AGGTTTTGTA | 85 | TGAA | H1, H2, H3 |
|  |  |  | Sp-WT | 14N2 | AGATTTGAAGG AAAGGTTTTG | 86 | ATGAAT | H1, H2, H3 |
| 15 | * |  | Sp-VRQR | 15N1 | TTTGAAGGAA AGGTTTTGTA | 87 | TGAA | H1, H2, H3 |
|  |  |  | Sp-VRQR | 15N2 | AGATTTGAAGG AAAGGTTTTG | 88 | ATGAAT | H1, H2, H3 |

Cloning of Cas9 and sgRNA Expression Constructs

All Cas9 expression plasmids were constructed into a CAG-Cas9-T2A-EGFP backbone modified from a pSQT817 vector (Addgene #53373). EGFP and Cas9 were co-expressed as a single protein before being separated by a self-cleaving T2A peptide; EGFP served as the marker for the targeted cells and for the downstream FACS sorting. The sgRNAs for wild-type and variant SpCas9 were cloned into the expression vector BPK1520 (Addgene #65777), and the sgRNAs for wild-type and variant SaCas9 were cloned into the BPK2660 vector (Addgene #70709).

Characterization of Human Cell Lines

We sourced and genotyped several human cell-lines to serve as homozygous and heterozygous RP1 haplotypes to evaluate the targeting allele-specificity and efficiency of our sgRNAs. These include HEK293T (H2/H3), ARPE-19 (H1/H2), hTERT RPE-1 (H3/H3), Min38931 fibroblast (H2/H2 from RP1 patient), HL-60 (H1/H1), HT-1080 (H1/H2), C3A (H2/H3), Y79 (H1/H3) Weri-Rb1 (H1/H2) and the haploid human cell-line HAP1 (H1).

HEK293T cells were selected for the initial screening step, for their efficiency of transfection, and heterozygous H2/H3 haplotype, such that all sgRNAs could be tested in these cells (in the H3 positions, H2 SNPs are the same as H1, and vice versa. Thus the reference haplotype H1 has 13 targetable sites, H2 has 10 sites, and H3 has 3 sites).

To assess the efficiency and specificity of each gRNA, we co-transfected CAG-Cas9-T2A-EGFP and sgRNA plasmids into HEK293T cells via Lipofectamine 3000. Transfection of the Cas9-EGFP plasmid alone was included as a negative control. Cells were collected 2 days after transfection, followed by FACS sorting. Genomic DNA was isolated from the sorted EGFP positive cells, PCR amplified, followed by NGS deep sequencing.

Measurement of On-Target Efficiency

NGS deep sequencing was utilized to quantitatively analyze the specific DSBs-NHEJ events in the genome, and to predict the cleavage specificity. Briefly, short PCR products spanning the targeted site were amplified and purified, and dual-indexed TruSeq 250 bp paired end sequencing was performed on an Illumina MiSeq Sequencer by MGH CCIB. Paired-end reads were mapped to the human genome reference and reads with an average quality score >30 were analyzed for indels that overlap the intended target nuclease binding site. Indel analyses were conducted using an in-house algorithm at the MGH CCIB.

Figure 2A:
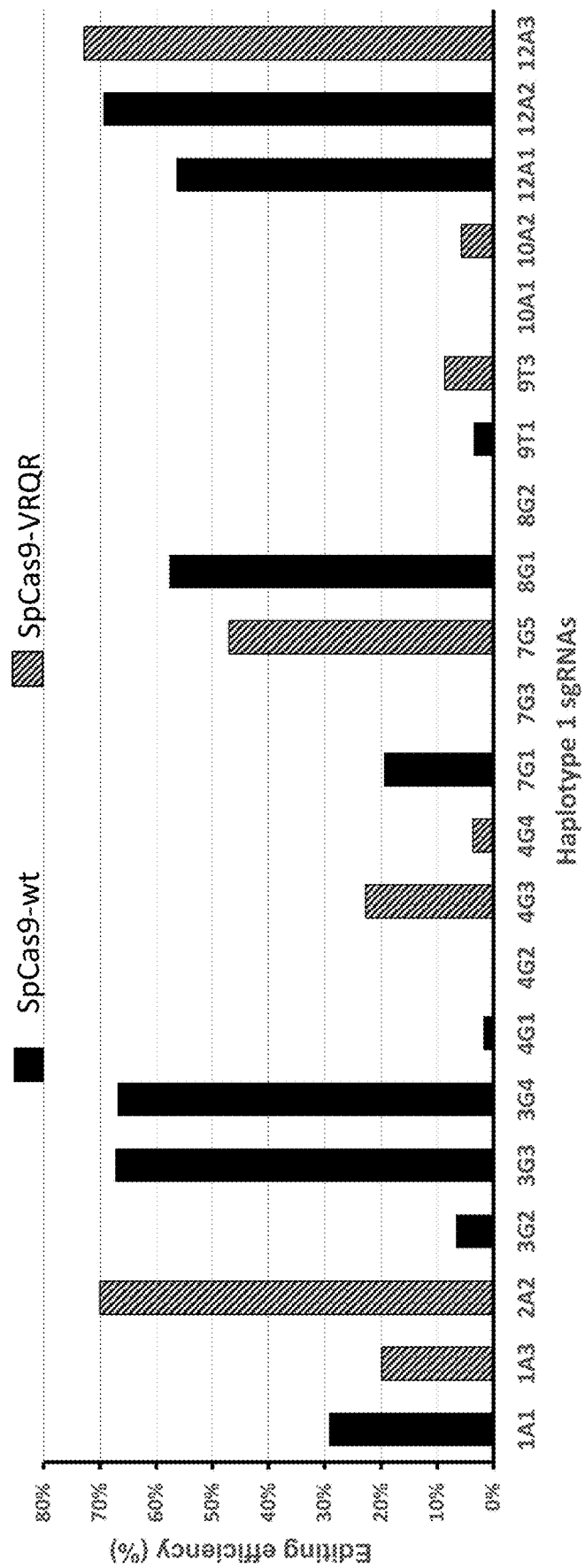
FIGS. 2A-2B show editing efficiencies of RP1 gRNAs in cultured human cells.
Figure 2B:
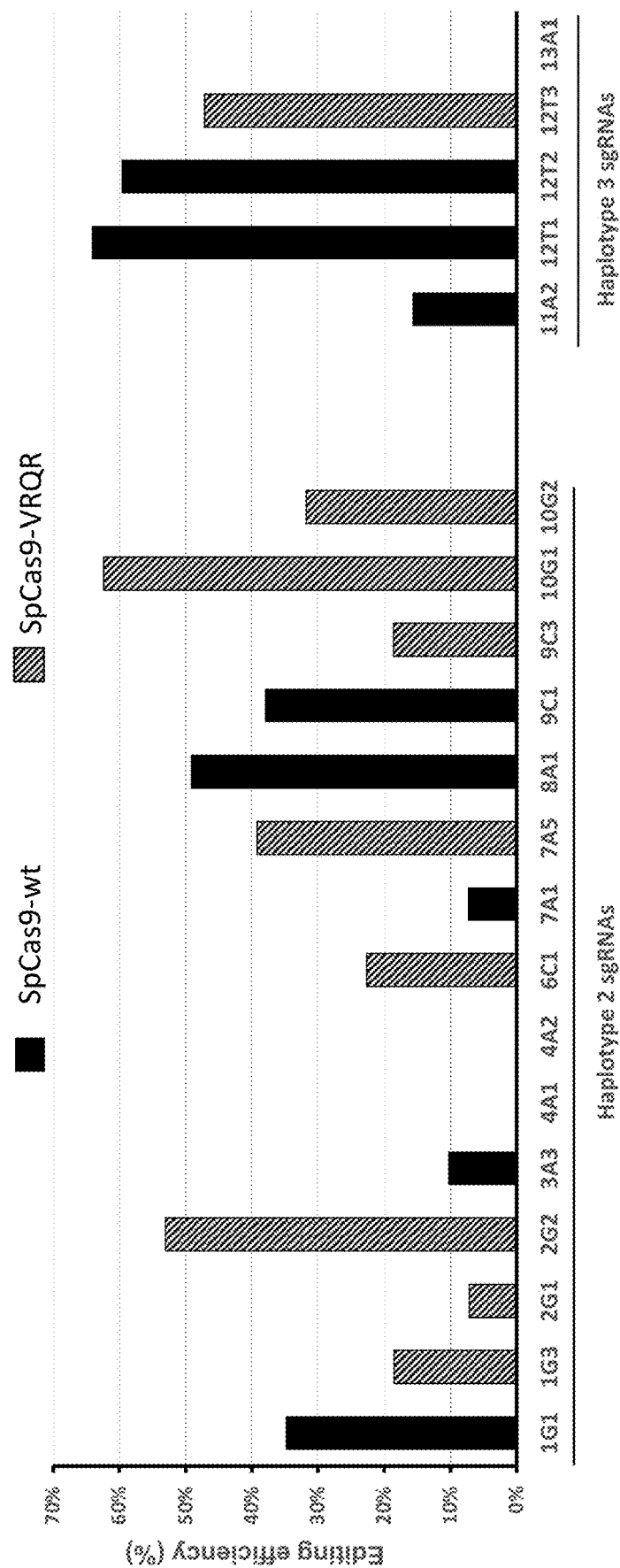

SpCas9 wild-type and variant guides for all three haplotypes have been tested in HEK293T, ARPE19, hTert-RPE1, U20S, HAP1 and Weri-Rb1 cell lines, and analyzed for edited and unedited reads per allele. Editing efficiency was calculated as a ratio of edited alleles/total reads per allele, and are presented in Table 7 below, and FIGS. 2A and 2B.

TABLE 7

Indel rate of gRNAs targeting RP1 haplotypes

| Sites # | SNPs | SNP | RP1 | sgRNA ID | Editing on H1 | Editing on H2 | Editing on H3 |
|---|---|---|---|---|---|---|---|
| 1 | rs702761 | A > G | Intron 1 | 1A1 and 1G1 | 29.2% | 34.9% | |
| | | | | 1A2 and 1G2 | | | |
| | | | | 1A3 and 1G3 | 19.9% | 18.6% | |
| | | | | 1A4 and 1G4 | 0.0% | 0.0% | |
| | | | | 1A5 and 1G5 | 61.7% | 43.3% | |
| | | | | 1A6 and 1G6 | 0.0% | 3.5% | |
| 2 | rs145290 | A > G | Intron 1 | 2G1 | | 7.2% | |
| | | | | 2A2 and 2G2 | 70.0% | 53.1% | |
| | | | | 2A3 and 2G3 | | | |
| | | | | 2A4 and 2G4 | 0.0% | 0.0% | |
| | | | | 2A5 and 2G5 | 0.0% | 0.0% | |
| 3 | rs436527 | G > A | Intron 1 | 3G/A1 | | | |
| | | | | 3G2 | 6.7% | | |
| | | | | 3G3 and 3A3 | 67.3% | 10.4% | |
| | | | | 3G4 and 3A4 | 66.9% | | |
| | | | | 3G5 and 3A5 | | | |
| | | | | 3G6 and 3A6 | 24.2% | 28.9% | |
| | | | | 3G7 and 3A7 | 2.9% | 0.0% | |
| 4 | rs428854 | G > A | Intron 3 | 4G1 and 4A1 | 1.8% | 0.0% | |
| | | | | 4G2 and 4A2 | 0.0% | 0.0% | |
| | | | | 4G3 and 4A3 | 22.8% | | |
| | | | | 4G4 and 4A4 | 3.6% | | |
| | | | | 4G5 and 4A5 | 6.2% | 0.0% | |
| | | | | 4A6 | | | |
| 5 | rs424499 | T > C | Intron 3 | 5T1 and 5C1 | | | |
| | | | | 5T2 and 5C2 | | | |
| | | | | 5T3 and 5C3 | | | |
| | | | | 5T4 and 5C4 | | | |
| | | | | 5C5 | | | |
| 6 | rs429668 | T > C | Intron 3 | 6C1 | | 22.6% | |
| 7 | rs444772 | G > A | Exon 4 | 7G1 and 7A1 | 19.5% | 7.4% | |
| | | | | 7G2 and 7A2 | | | |
| | | | | 7G3 and 7A3 | 0.4% | | |
| | | | | 7G4 and 7A4 | | | |
| | | | | 7G5 and 7A5 | 47.0% | 39.2% | |
| | | | | 7G6 and 7A6 | | | |
| | | | | 7G7 and 7A7 | | | |
| 8 | rs446227 | G > A | Exon 4 | 8G1 and 8A1 | 57.7% | 49.2% | |
| | | | | 8G2 and 8A2 | | | |
| | | | | 8G3 and 8A3 | 0.0% | | |
| 9 | rs414352 | T > C | Exon 4 | 9T1 and 9C1 | 3.5% | 38.0% | |
| | | | | 9T2 and 9C2 | | | |
| | | | | 9T3 and 9C3 | 8.7% | 18.6% | |
| | | | | 9T4 and 9C4 | | | |
| | | | | 9T5 and 9C5 | | | |
| | | | | 9T6 and 9C6 | | | |
| 10 | rs441800 | A > G | Exon 4 | 10A1 and 10G1 | 0.0% | 62.4% | |
| | | | | 10A2 and 10G2 | 5.7% | 31.8% | |
| | | | | 10G3 | | | |
| | | | | 10A4 and 10G4 | | | |
| | | | | 10A5 and 10G5 | | | |
| | | | | 10A6 and 10G6 | | | |
| | | | | 10A7 and 10G7 | | | |
| 11 | rs62514616 | G > A | Intron 3 | 11G1 and 11A1 | | | |
| | | | | 11G2 and 11A2 | | | 15.7% |
| | | | | 11G3 and 11A3 | | | |
| | | | | 11A4 | | | |
| 12 | rs2293869 | A > T | Exon 4 | 12A1 and 12T1 | 56.4% | | 64.1% |
| | | | | 12A2 and 12T2 | 69.4% | | 59.7% |
| | | | | 12A3 and 12T3 | 72.8% | | 47.2% |
| | | | | 12A4 | | | |
| 13 | rs61739567 | G > A | Exon 4 | 13G1 and 13A1 | | | 0.0% |
| | | | | 13G2 and 13A2 | | | |
| 14 | wt | — | Intron 3 | 14N1 | 95.2% | | |
| | | — | | 14N2 | 88.7% | | |
| 15 | wt | — | Intron 3 | 15N1 | 51.6% | | |
| | | — | | 15N2 | 35.0% | | |

Specific Knockout of RP1 Alleles by Cas9-sgRNA sgRNAs with the highest targeting efficiency and specificity were selected, and their ability to target and knockout RP1 alleles via paired sgRNA directed editing in heterozygous or haploid cell lines was evaluated. Paired guide deletion strategies for H1 were first tested. Editing by a single gRNA targeted to an intronic region was repaired by NHEJ, and did not affect RP1 expression (FIG. 4, single guide 14N2 only), therefore highly efficient guides targeting regions of intron 3 in any allele were paired with allele-specific sgRNAs targeting H1 SNPs in intron 1, or exon 4. Note that the bi-allele targeting guides will edit both wild type and mutant alleles, but when paired with allele specific guides in intron 1, or exon 4, will delete a large genomic portion form the mutant allele only. Larger deletions are also possible via the pairing of allele specific guides in intron 1 and exon 4 (Table 8 and Table 9).

TABLE 8

Possible combinations of sgRNAs to target H1/H2, H3/H2 heterozygous

| Intron 1 | Intron 3 | Exon 4 |
| --- | --- | --- |
| 1A1 and 1G1 | 14N1 | 10A2 and 10G2 |
| 1A5 and 1G5 | 14N2 | 7G1 and 7A1 |
| 2A2 and 2G2 | 15N1 | 7G5 and 7A5 |
| 3G3 and 3A3 | 15N2 | 8G1 and 8A1 |
| 3G4 and 3A4 | 4G3 | 9T1 and 9C1 |
| 3G6 and 3A6 | 5C5 | 9T3 and 9C3 |

TABLE 9

Possible combinations of sgRNAs to target H1/H3 heterozygous

| Intron 3 | Exon 4 |
| --- | --- |
| 14N1 | 12A1 and 12T1 |
| 14N2 | 12A2 and 12T2 |
| 15N1 | 12A3 and 12T3 |
| 15N2 | |

Quantification of Genomic Editing-qPCR Strategy

Figure 3:
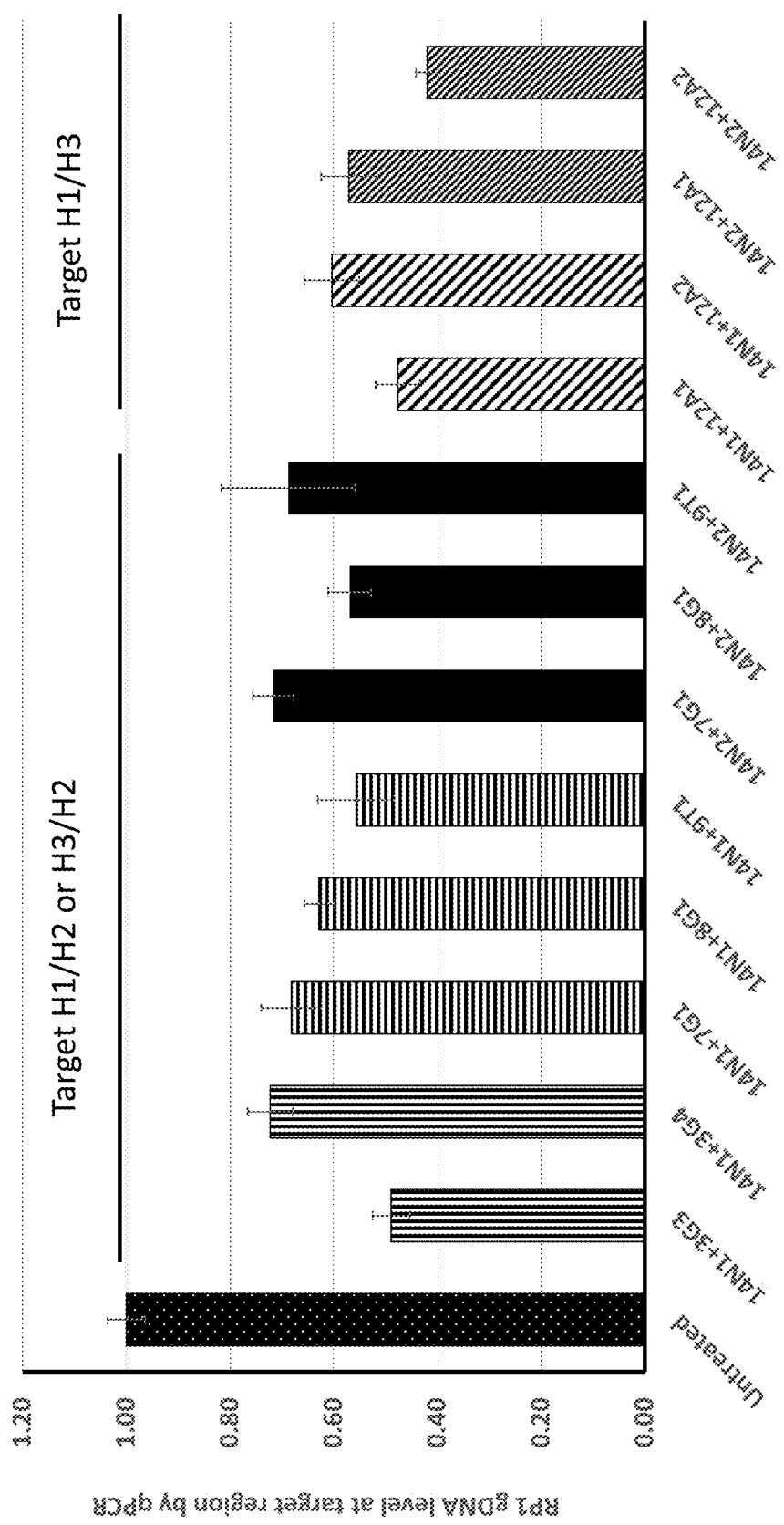
FIG. 3 shows quantification of genomic deletion in HAP-1 cells treated with pairs of sgRNAs targeting RP1 haplotype 1. Amplicons within the predicted deletion region were quantified by qPCR, relative to unedited samples. Deletion efficiency was calculated from the reduction in amplicon quantity.

A qPCR strategy was developed to quantify editing and RP1 allele deletion efficiency at the genomic level. qPCR primers were designed to amplify regions within the predicted deletion. The 'internal' amplicon was produced only from remaining 'undeleted' alleles, and after normalization to a reference gene on another chromosome, the remaining 'undeleted' allele was quantified relative to unedited cells (FIG. 3). All combinations for sgRNAs tested were able to decrease RP1 allele content in edited cells, up to 58% for 14N2+12A2 gRNA pair. However, this quantification strategy may not capture all editing events. For example, inversions after dual DSBs may still allow amplification of 'internal' amplicons, if they have not been damaged by editing. Quantification of a reduction of RP1 expression is a more accurate measure of allele disruption, as described below.

Quantification of RP1 Expression after Editing with Dual sgRNAs

Figure 4:
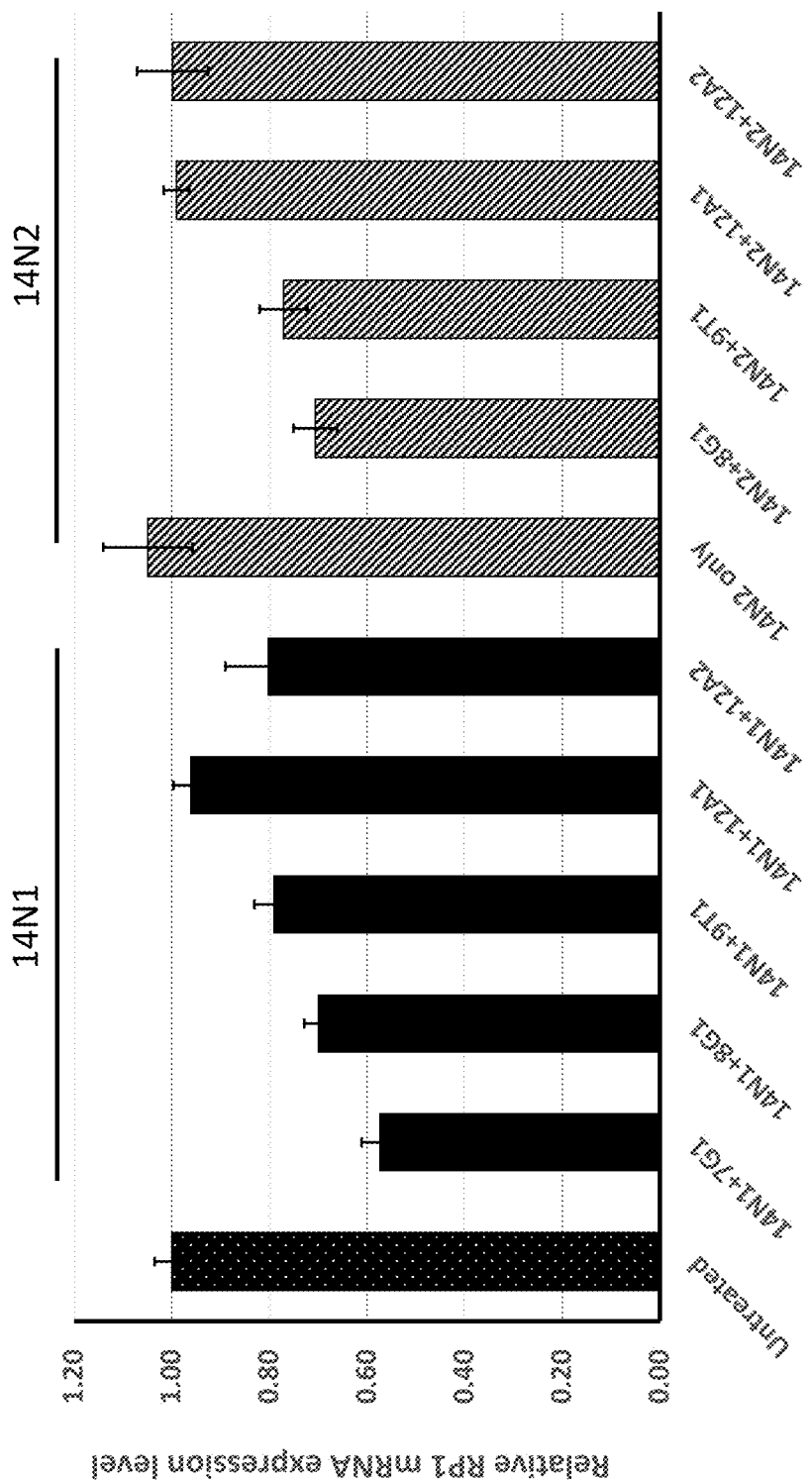
FIG. 4 shows quantification of RP1 expression by qRT-PCR in Weri-Rb1 cells treated with pairs of sgRNAs targeting RP1 haplotype 1. Specific pairs of sgRNAs were able to decrease endogenous RP1 expression in heterozygous (H1/H2) Weri-Rb1 cells.

Dual sgRNAs were transfected into the RP1 expressing cell-line Weri-Rb1. RNA was extracted from the GFP+ cell fraction with RNeasy Micro Plus (Qiagen), and cDNA libraries were generated for each sample with Superscript III First-Strand Synthesis SuperMix for qRT-PCR (Invitrogen). The sequences of cDNA specific primers for RP1, and the reference gene GAPDH, were obtained from OriGene, and RP1 expression was quantified in edited samples relative to non-transfected control cells (FIG. 4). A reduction in RP1 expression of 43% was observed in cells edited with 14N1+7G1 gRNAs. No change in RP1 expression was observed when the universal intron3 targeting guide 14N2 was individually tested.

Generation of RP1 Expressing Cell-Lines

Figure 5A:
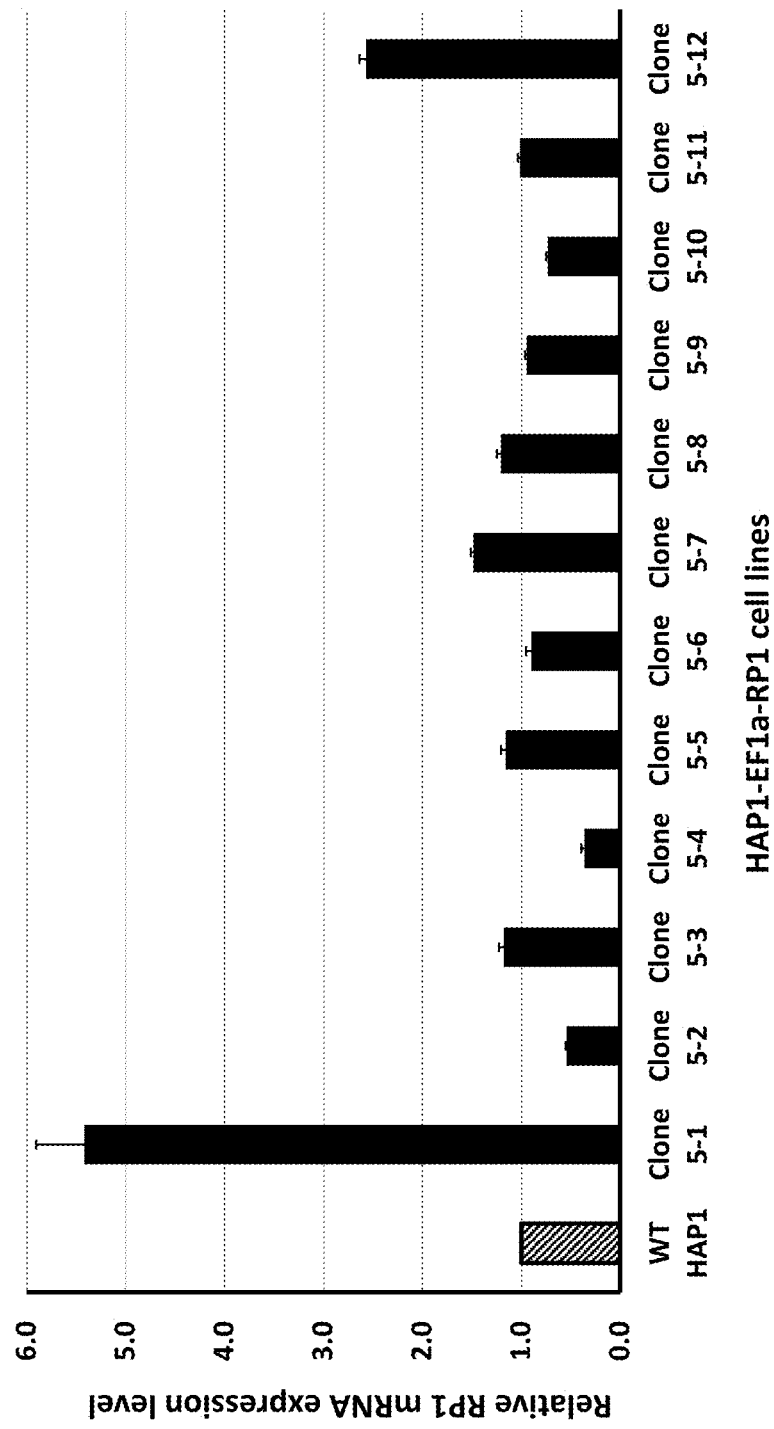
FIGS. 5A-5B show generation of RP1 expression cell lines.
Figure 5B:
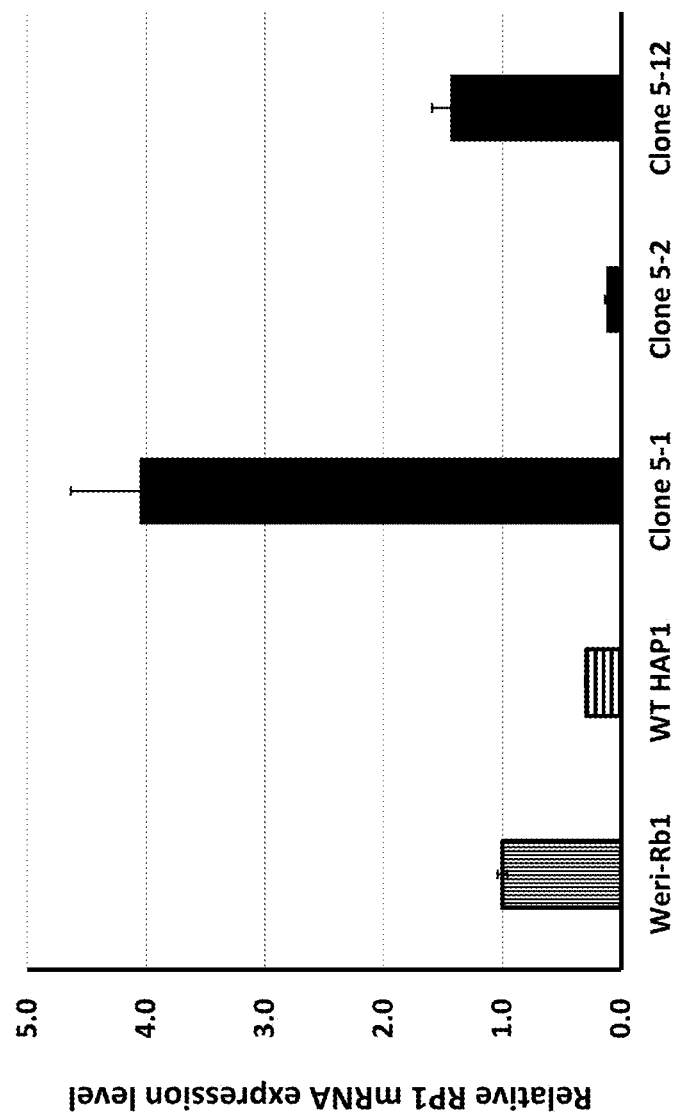

There are few commercially available cell lines in which to test the effect of our editing strategy on RP1 expression, since RP1 is specifically expressed in specialized post-mitotic photoreceptors. The retinoblastoma cell line Weri-Rb1 expresses low levels of RP1, but is difficult to transfect. Cell-lines were therefore generated with exogenous expression of RP1, by insertion of a promoter upstream of the RP1 transcriptional start site (TSS). A plasmid encoding 100 bp homology arms and the EF1a promoter followed by a neomycin resistance gene and a P2A peptide cleavage motif, was co-transfected with plasmids which express an RP1 targeting sgRNA, and SpCas9, into wild-type Hap1 cells. After 3 weeks of G418 selection at 50 ug/mL, 15 individual colonies were picked and analyzed for targeted genomic integration of the promoter cassette, and for RP1 expression by semi-quantitative RT-PCR. Clone 5 was then selected for stable cell line generation from single cells, and 12 clones were tested for relative RP1 expression by qRT-PCR (FIG. 5A). Three cell lines were then quantified for RP1 expression relative to the endogenously expressing cell line Weri-Rb1 (FIG. 5B). Clone 5-1 exhibited a four-fold increase in RP1 expression compared to Weri-Rb1, and is used to evaluate editing efficiency of the pairs of sgRNAs, and their effect on RP1 expression.

iPSCs have also been generated from fibroblasts obtained from two RP1 patients (OGI1557-002771 and OGI1781-003109) with dominant mutations selected from the probands in the IRD Biobank at MEEI. Patient OGI1557-002771 is heterozygous for H1/H3 haplotype, and carries the c. 2103delAATA mutation in cis with the SNPs for H3. Patient OGI1781-003109 is heterozygous for H2/H3, and carries the mutation c.2029C>T in cis with the SNPs for H2. Cells have undergone reprogramming with the non-integrating Sendaii virus method at Harvard iPSC Core Facility. These iPS cells and the differentiated retinal organoids are used to evaluate the lead Cas9/dual sgRNA pairs regarding their efficacy and safety.

Table 10 presents a summary of the SNPs and their presence in each haplotype, with the genomic information included.

TABLE 10

RP1 Haplotype SNPs with Genomic Location.

| | RP1 Haplotype variant | | | Genome |
| --- | --- | --- | --- | --- |
| SNP | H1 | H2 | H3 | location |
| rs702761 | A | G | A | Intron 1 |
| rs145290 | A | G | A | Intron 1 |
| rs436527 | G | A | G | Intron 1 |
| rs428854 | G | A | G | Intron 3 |
| rs424499 | T | C | T | Intron 3 |
| rs429668 | T | C | T | Intron 3 |
| rs62514616 | G | G | A | Intron 3 |
| rs444772 | G | A | G | Exon 4 |
| rs446227 | G | A | G | Exon 4 |
| rs414352 | T | C | T | Exon 4 |
| rs441800 | A | G | A | Exon 4 |
| rs2293869 | A | A | T | Exon 4 |
| rs61739567 | G | G | A | Exon 4 |

Table 11 presents a summary of first and second gRNA targets by haplotype.

TABLE 11

First and Second gRNA Targets by Haplotype.

| Human subject RP1 haplotype | RP1 mutant allele | First gRNA target | Second gRNA target |
|---|---|---|---|
| H1/H2 | H1 | rs702761A, or rs145290A, or rs436527G | rs428854G, or rs424499T, or rs429668T, or rs444772G, or rs446227G, or rs414352T, or rs441800A |
| | | rs428854G, or rs424499T, or rs429668T | rs444772G, or rs446227G, or rs414352T, or rs441800A |
| | H2 | rs702761G, or rs145290G, or rs436527A | rs428854A, or rs424499C, or rs429668C, or rs444772A, or rs446227A, or rs414352C, or rs441800G |
| | | rs428854A, or rs424499C, or rs429668C | rs444772A, or rs446227A, or rs414352C, or rs441800G |
| H2/H3 | H2 | rs702761G, or rs145290G, or rs436527A | rs428854A, or rs424499C, or rs429668C, or rs62514616A, or rs444772A, or rs446227A, or rs414352C, or rs441800G, or rs2293869T, or rs61739567A |
| | | rs428854A, or rs424499C, or rs429668C, or rs62514616A | rs444772A, or rs446227A, or rs414352C, or rs441800G, or rs2293869T, or rs61739567A |
| | H3 | rs702761A, or rs145290A, or rs436527G | rs428854G, or rs424499T, or rs429668T, or rs62514616G, or rs444772G, or rs446227G, or rs414352T, or rs441800A, or rs2293869A, or rs61739567G |
| | | rs428854G, or rs424499T, or rs429668T, or rs62514616G | rs444772G, or rs446227G, or rs414352T, or rs441800A, or rs2293869A, or rs61739567G |
| H1/H3 | H1 | rs62514616G | rs2293869A, or rs61739567G |
| H1/H3 | H3 | rs62514616A | rs2293869T, or rs61739567A |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A composition comprising (a) a nucleic acid comprising a sequence encoding a RNA-guided nuclease (RGN) or a variant thereof, and (b) nucleic acids comprising sequences encoding a first guide RNA (gRNA) and a second gRNA, wherein the first and second gRNAs target haplotype variants on the same allele of an human RP1 gene, and wherein the first and second gRNAs both target linked variants in haplotype H1, or H2, or H3, wherein:

(i) the first gRNA is targeted to a single nucleotide polymorphism (SNP) in intron 1 of an RP1 gene of a human subject selected from rs702761, rs145290, and rs436527, and the second is targeted to a SNP selected from rs428854, rs424499, and rs429668 in intron 3, or a SNP selected from rs444772, rs446227, rs414352, rs441800, rs2293869, and rs61739567 in exon 4 of the same haplotype of an human RP1 gene, or (ii) the first gRNA is targeted to a SNP selected from rs428854, rs424499, rs429668, and rs62514616 in intron 3 of an RP1 gene of a human subject; and the second gRNA is targeted to a SNP selected from rs444772, rs446227, rs414352, rs441800, rs2293869, and rs61739567 in exon 4 of the same haplotype of an human RP1 gene, and wherein the haplotypes H1, H2, and H3 are:

| SNP | RP1 Haplotype variant | | | Genome location |
|---|---|---|---|---|
| | H1 | H2 | H3 | |
| rs702761 | A | G | A | Intron 1 |
| rs145290 | A | G | A | Intron 1 |
| rs436527 | G | A | G | Intron 1 |
| rs428854 | G | A | G | Intron 3 |
| rs424499 | T | C | T | Intron 3 |
| rs429668 | T | C | T | Intron 3 |
| rs62514616 | G | G | A | Intron 3 |
| rs444772 | G | A | G | Exon 4 |
| rs446227 | G | A | G | Exon 4 |
| rs414352 | T | C | T | Exon 4 |
| rs441800 | A | G | A | Exon 4 |
| rs2293869 | A | A | T | Exon 4 |
| rs61739567 | G | G | A | Exon 4. |

2. The composition of claim 1, wherein one or both gRNAs comprise a protospacer sequence of one of SEQ ID NOs:22-88.

3. The composition of claim 1, wherein the RGN is *S. aureus* Cas9 or *S. pyogenes* Cas9 or a variant thereof.

4. The composition of claim 3, wherein the Cas9 comprises a nuclear localization signal, optionally a C-terminal nuclear localization signal and/or an N-terminal nuclear localization signal; and/or wherein the sequence encoding Cas9 comprises a polyadenylation signal.

5. The composition of claim 3, wherein the Cas9 protein is *S. aureus* Cas9 or a variant thereof and the first and/or the second gRNA is a unimolecular *S. aureus* gRNA comprising SEQ ID NO: 1 or SEQ ID NO: 2, or the corresponding two-part modular *S. aureus* gRNA, wherein the crRNA component comprises SEQ ID NO: 3 or SEQ ID NO: 4 and the tracrRNA component comprises SEQ ID NO: 5 or SEQ ID NO: 6.

6. The composition of claim 5, wherein the Cas9 protein is *S. pyogenes* Cas9, or a variant thereof, and the first and/or the second gRNA is an *S. pyogenes* gRNA comprising any one of the sequences set forth in SEQ ID NOs: 7-16.

7. The composition of claim 1, which is comprised in one or more viral delivery vectors.

8. The composition of claim 7, wherein the viral delivery vectors comprise a promoter operably linked to the RGN, wherein the promoter is selected from cytomegalovirus (CMV), chicken β-actin (CBA), cytomegalovirus (CMV) enhancer fused to the chicken beta-actin promoter (CAG), CBh, elongation factor alpha 1 (EFalpha1), EF-1 Alpha Short (EFS), CASI, RHO, beta phosphodiesterase (PDE), retinitis pigmentosa (RP1), rhodopsin kinase (hGRK1), or cone arrestin (CAR) promoter.

9. The composition of claim 7, wherein the viral delivery vectors are adeno-associated virus (AAV) vectors.

10. The composition of claim 9, wherein the viral delivery vectors comprise a first and a second inverted terminal repeat sequence (ITR) and;
 (i) sequences encoding one or both of the first guide RNA (gRNA) and the second gRNA, and
  a U6 promoter for driving expression of the first and/or second gRNAs; and/or
 (ii) a sequence encoding the RGN or variant thereof, and
  a promoter operably linked to the RGN.

11. The composition of claim 10, wherein the promoter is selected from the group consisting of a CMV, an EFS, or an hGRK1, EFalpha1, or RP1 promoter.

12. The composition of claim 1, wherein (a) and (b) are in a single viral delivery vector or in separate viral delivery vectors.

13. The composition of claim 1, wherein the first gRNA target and second gRNA target comprise:

| Human subject RP1 haplotype | RP1 mutant allele | First gRNA target | Second gRNA target |
|---|---|---|---|
| H1/H2 | H1 | rs702761A, or rs145290A, or rs436527G | rs428854G, or rs424499T, or rs429668T, or rs444772G, or rs446227G, or rs414352T, or rs441800A |
|  |  | rs428854G, or rs424499T, or rs429668T | rs444772G, or rs4462276, or rs4143521, or rs441800A |
|  | H2 | rs702761G, or rs145290G, or rs436527A | rs428854A, or rs424499C, or rs429668C, or rs444772A, or rs446227A, or rs414352C, or rs441800G |
|  |  | rs428854A, or rs424499C, or rs429668C | rs444772A, or rs446227A, ar rs414352C, or rs441800G |
| H2/H3 | H2 | rs702761G, or rs145290G, or rs4365274 | rs428854A, or rs424499C, or rs429668C, or rs62514616A, or rs444772A, or rs446227A, or rs414352C, or rs441800G, of rs2293869T, or rs61739567A |
|  |  | rs428854A, or rs424499C, or rs429668C, or rs62514616A | rs444772A, or rs446227A, or rs414352C, or rs441800G, or rs2293869T, or rs61739567A |
|  | H3 | rs702761A, orrs145290A, or rs4365276 | rs428854G, or rs424499T, or rs429668T, or rs62514616G, or rs444772G, or rs446227G, or rs414352T, or rs441800A, or rs2293869A, or rs61739567G |
|  |  | rs4288546, or rs424499T, or rs429668T, or rs62514616G | rs444772G, or rs446227G, or rs414352T, or rs441800A, or rs2293869A, or rs61739567G |
| H1/H3 | H1 | rs625146166 | rs2293869A, or rs61739567G |
| H1/H3 | H3 | rs62514616A | rs2293869T, or rs61739567A. |

* * * * *

UNITED STATES PATENT AND TRADEMARK OFFICE
CERTIFICATE OF CORRECTION

Page 1 of 1

PATENT NO. : 12,129,496 B2
APPLICATION NO. : 17/175234
DATED : October 29, 2024
INVENTOR(S) : Qin Liu and Caitlin Collin It is certified that error appears in the above-identified patent and that said Letters Patent is hereby corrected as shown below:

In the Claims

In Column 63, Line 48, Claim 1, delete "second" and insert -- second gRNA --

In Column 65, Line 4, Claim 6, delete "claim 5," and insert -- claim 3, --

In Column 65, Line 17 (approx.), Claim 8, delete "rhodopsin kinase" and insert -- human rhodopsin kinase --

In Column 66, Line 3, Claim 10, delete "claim 9," and insert -- claim 7, --

In Columns 65-66, Line 10, Claim 13, delete "rs4462276, or rs4143521," and insert -- rs446227G, or rs414352T, --

In Columns 65-66, Line 15, Claim 13, delete "ar" and insert -- or --

In Columns 65-66, Line 18, Claim 13, delete "rs4365274" and insert -- rs436527A --

In Columns 65-66, Line 19, Claim 13, delete "of" and insert -- or --

In Columns 65-66, Line 24, Claim 13, delete "orrs145290A," and insert -- or rs145290A, --

In Columns 65-66, Line 25, Claim 13, delete "rs4365276" and insert -- rs436527G --

In Columns 65-66, Line 28, Claim 13, delete "rs4288546," and insert -- rs428854G, --

In Columns 65-66, Line 31, Claim 13, delete "rs625146166" and insert -- rs62514616G --

Signed and Sealed this
Third Day of June, 2025

Coke Morgan Stewart
*Acting Director of the United States Patent and Trademark Office*

SEQUENCE LISTING

<160> NUMBER OF SEQ ID NOS: 88

<210> SEQ ID NO 1
<211> LENGTH: 102
<212> TYPE: DNA
<213> ORGANISM: Staphylococcus aureus
<220> FEATURE:
<221> NAME/KEY: misc_feature
<222> LOCATION: (1)..(20)
<223> OTHER INFORMATION: Targeting domain of 16-24 nts, each n=A, C, T, G, unknown or other

<400> SEQUENCE: 1
nnnnnnnnnn nnnnnnnnnn gttttagtac tctggaaaca gaatctacta aaacaaggca    60
aaatgccgtg tttatctcgt caacttgttg gcgagatttt tt    102

<210> SEQ ID NO 2
<211> LENGTH: 102
<212> TYPE: DNA
<213> ORGANISM: Staphylococcus aureus
<220> FEATURE:
<221> NAME/KEY: misc_feature -continued

```
<222> LOCATION: (1)..(20)
<223> OTHER INFORMATION: Targeting domain of 16-24 nts, each n=A, C, T,
      G, unknown or other

<400> SEQUENCE: 2
nnnnnnnnnn nnnnnnnnnn gttatagtac tctggaaaca gaatctacta taacaaggca      60
aaatgccgtg tttatctcgt caacttgttg gcgagatttt tt                         102

<210> SEQ ID NO 3
<211> LENGTH: 14
<212> TYPE: DNA
<213> ORGANISM: Staphylococcus aureus

<400> SEQUENCE: 3
gttttagtac tctg                                                        14

<210> SEQ ID NO 4
<211> LENGTH: 14
<212> TYPE: DNA
<213> ORGANISM: Staphylococcus aureus

<400> SEQUENCE: 4
gttatagtac tctg                                                        14

<210> SEQ ID NO 5
<211> LENGTH: 64
<212> TYPE: DNA
<213> ORGANISM: Staphylococcus aureus

<400> SEQUENCE: 5
cagaatctac taaaacaagg caaaatgccg tgtttatctc gtcaacttgt tggcgagatt      60
tttt                                                                   64

<210> SEQ ID NO 6
<211> LENGTH: 64
<212> TYPE: DNA
<213> ORGANISM: Staphylococcus aureus

<400> SEQUENCE: 6
cagaatctac tataacaagg caaaatgccg tgtttatctc gtcaacttgt tggcgagatt      60
tttt                                                                   64

<210> SEQ ID NO 7
<211> LENGTH: 32
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: n is A, C, U, G, unknown, or other and this
      region may encompass 17-20 nucleotides

<400> SEQUENCE: 7
nnnnnnnnnn nnnnnnnnnn guuuuagagc ua                                    32

<210> SEQ ID NO 8
<211> LENGTH: 42
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: n is A, C, U, G, unknown, or other and this
      region may encompass 17-20 nucleotides
```

```
<400> SEQUENCE: 8
nnnnnnnnnn nnnnnnnnnn guuuuagagc uaugcuguuu ug                 42

<210> SEQ ID NO 9
<211> LENGTH: 36
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: N is A, C, U, G, unknown, or other and this
      region may encompass 17-20 nucleotides

<400> SEQUENCE: 9
nnnnnnnnnn nnnnnnnnnn guuuuagagc uaugcu                        36

<210> SEQ ID NO 10
<211> LENGTH: 62
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: N is A, C, U, G, unknown, or other and this
      region may encompass 17-20 nucleotides

<400> SEQUENCE: 10
nnnnnnnnnn nnnnnnnnnn guuuuagagc uagaaauagc aaguuaaaau aaggcuaguc    60
cg                                                             62

<210> SEQ ID NO 11
<211> LENGTH: 75
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: N is A, C, U, G, unknown, or other and this
      region may encompass 17-20 nucleotides

<400> SEQUENCE: 11
nnnnnnnnnn nnnnnnnnnn guuuuagagc uaugcugaaa agcauagcaa guuaaaauaa    60
ggcuaguccg uuauc                                               75

<210> SEQ ID NO 12
<211> LENGTH: 87
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: N is A, C, U, G, unknown, or other and this
      region may encompass 17-20 nucleotides

<400> SEQUENCE: 12
nnnnnnnnnn nnnnnnnnnn guuuuagagc uaugcuguuu uggaaacaaa acagcauagc    60
aaguuaaaau aaggcuaguc cguuauc                                  87

<210> SEQ ID NO 13
<211> LENGTH: 96
<212> TYPE: RNA
<213> ORGANISM: Streptococcus pyogenes
<220> FEATURE:
<221> NAME/KEY: misc_feature
<222> LOCATION: (1)..(20)
```

```
<223> OTHER INFORMATION: N is A, C, U, G, unknown, or other and this
      region may encompass 17-20 nucleotides

<400> SEQUENCE: 13
nnnnnnnnnn nnnnnnnnnn guuuuagagc uagaaauagc aaguuaaaau aaggcuaguc    60
cguuaucaac uugaaaaagu ggcaccgagu cggugc                              96

<210> SEQ ID NO 14
<211> LENGTH: 96
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: N is A, C, U, G, unknown, or other and this
      region may encompass 17-20 nucleotides

<400> SEQUENCE: 14
nnnnnnnnnn nnnnnnnnnn guuuaagagc uagaaauagc aaguuuaaau aaggcuaguc    60
cguuaucaac uugaaaaagu ggcaccgagu cggugc                              96

<210> SEQ ID NO 15
<211> LENGTH: 106
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: N is A, C, U, G, unknown, or other and this
      region may encompass 17-20 nucleotides

<400> SEQUENCE: 15
nnnnnnnnnn nnnnnnnnnn guuuuagagc uaugcuggaa acagcauagc aaguuuaaau    60
aaggcuaguc cguuaucaac uugaaaaagu ggcaccgagu cggugc                  106

<210> SEQ ID NO 16
<211> LENGTH: 106
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: N is A, C, U, G, unknown, or other and this
      region may encompass 17-20 nucleotides

<400> SEQUENCE: 16
nnnnnnnnnn nnnnnnnnnn guuuaagagc uaugcuggaa acagcauagc aaguuuaaau    60
aaggcuaguc cguuaucaac uugaaaaagu ggcaccgagu cggugc                  106

<210> SEQ ID NO 17
<211> LENGTH: 7
<212> TYPE: PRT
<213> ORGANISM: Artificial Sequence
<220> FEATURE:
<223> OTHER INFORMATION: SV40 large T antigen NLS

<400> SEQUENCE: 17

Pro Lys Lys Lys Arg Arg Val
1               5

<210> SEQ ID NO 18
<211> LENGTH: 7
<212> TYPE: PRT
<213> ORGANISM: Artificial Sequence
<220> FEATURE:
```

```
<223> OTHER INFORMATION: SV40 large T antigen NLS

<400> SEQUENCE: 18

Pro Lys Lys Lys Arg Lys Val
1               5

<210> SEQ ID NO 19
<211> LENGTH: 18
<212> TYPE: PRT
<213> ORGANISM: Artificial Sequence
<220> FEATURE:
<223> OTHER INFORMATION: SV40 large T antigen NLS

<400> SEQUENCE: 19

Lys Arg Thr Ala Asp Gly Ser Glu Phe Glu Ser Pro Lys Lys Lys Arg
1               5                   10                  15

Lys Val

<210> SEQ ID NO 20
<211> LENGTH: 16
<212> TYPE: PRT
<213> ORGANISM: Artificial Sequence
<220> FEATURE:
<223> OTHER INFORMATION: nucleoplasmin NLS

<400> SEQUENCE: 20

Lys Arg Pro Ala Ala Thr Lys Lys Ala Gly Gln Ala Lys Lys Lys Lys
1               5                   10                  15

<210> SEQ ID NO 21
<211> LENGTH: 60
<212> TYPE: DNA
<213> ORGANISM: Artificial Sequence
<220> FEATURE:
<223> OTHER INFORMATION: polyadenylation signal

<400> SEQUENCE: 21
tagcaataaa ggatcgttta ttttcattgg aagcgtgtgt tggttttttg atcaggcgcg    60

<210> SEQ ID NO 22
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (15)..(15)
<223> OTHER INFORMATION: r is a, c, g, or t

<400> SEQUENCE: 22
atgctgatat tgaartagaa                                                20

<210> SEQ ID NO 23
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (14)..(14)
<223> OTHER INFORMATION: r is a or g

<400> SEQUENCE: 23
tgctgatatt gaartagaat                                                20
```

```
<210> SEQ ID NO 24
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (19)..(19)
<223> OTHER INFORMATION: r is a or g

<400> SEQUENCE: 24
caatatgctg atattgaart                                               20

<210> SEQ ID NO 25
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (22)..(22)
<223> OTHER INFORMATION: r is a or g

<400> SEQUENCE: 25
tcacaatatg ctgatattga ar                                            22

<210> SEQ ID NO 26
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (11)..(11)
<223> OTHER INFORMATION: r is a, c, g, or t

<400> SEQUENCE: 26
tgatattgaa rtagaatgga ac                                            22

<210> SEQ ID NO 27
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (22)..(22)
<223> OTHER INFORMATION: y is c or t

<400> SEQUENCE: 27
tgatactgaa gttccattct ay                                            22

<210> SEQ ID NO 28
<211> LENGTH: 20
<212> TYPE: DNA
<213> ORGANISM: Artificial Sequence
<220> FEATURE:
<223> OTHER INFORMATION: Protospacer

<400> SEQUENCE: 28
cattgtctaa ctttaggcaa                                               20

<210> SEQ ID NO 29
<211> LENGTH: 20
```

```
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (19)..(19)
<223> OTHER INFORMATION: r is a or g

<400> SEQUENCE: 29
tgtctaactt taggcaatra                                               20

<210> SEQ ID NO 30
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (8)..(8)
<223> OTHER INFORMATION: r is a or g

<400> SEQUENCE: 30
aggcaatraa gagtctctgc                                               20

<210> SEQ ID NO 31
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (22)..(22)
<223> OTHER INFORMATION: r is a or g

<400> SEQUENCE: 31
cattgtctaa ctttaggcaa tr                                            22

<210> SEQ ID NO 32
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (16)..(16)
<223> OTHER INFORMATION: y is c or t

<400> SEQUENCE: 32
tctgcagaga ctcttyattg cc                                            22

<210> SEQ ID NO 33
<211> LENGTH: 20
<212> TYPE: DNA
<213> ORGANISM: Artificial Sequence
<220> FEATURE:
<223> OTHER INFORMATION: Protospacer

<400> SEQUENCE: 33
acgtgtgagc caccacgccc                                               20

<210> SEQ ID NO 34
<211> LENGTH: 20
<212> TYPE: DNA
<213> ORGANISM: Artificial Sequence
<220> FEATURE:
```

```
<223> OTHER INFORMATION: Protospacer

<400> SEQUENCE: 34
cacgtgtgag ccaccacgcc                                              20

<210> SEQ ID NO 35
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (20)..(20)
<223> OTHER INFORMATION: y is c or t

<400> SEQUENCE: 35
ttaaataaga ctttaggccy                                              20

<210> SEQ ID NO 36
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (15)..(15)
<223> OTHER INFORMATION: y is c or t

<400> SEQUENCE: 36
taagacttta ggccygggcg                                              20

<210> SEQ ID NO 37
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (12)..(12)
<223> OTHER INFORMATION: y is c or t

<400> SEQUENCE: 37
gactttaggc cygggcgtgg                                              20

<210> SEQ ID NO 38
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (18)..(18)
<223> OTHER INFORMATION: r is a or g

<400> SEQUENCE: 38
tgtgagccac cacgcccrgg cc                                           22

<210> SEQ ID NO 39
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
```

```
<222> LOCATION: (19)..(19)
<223> OTHER INFORMATION: y is c or t

<400> SEQUENCE: 39
taaataagac tttaggccyg gg                                              22

<210> SEQ ID NO 40
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (17)..(17)
<223> OTHER INFORMATION: r is a or g

<400> SEQUENCE: 40
tttctgcttt cataaarcta                                                 20

<210> SEQ ID NO 41
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (16)..(16)
<223> OTHER INFORMATION: r is a or g

<400> SEQUENCE: 41
ttctgctttc ataaarctat                                                 20

<210> SEQ ID NO 42
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (9)..(9)
<223> OTHER INFORMATION: y is c or t

<400> SEQUENCE: 42
atccatagyt ttatgaaagc                                                 20

<210> SEQ ID NO 43
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (16)..(16)
<223> OTHER INFORMATION: y is c or t

<400> SEQUENCE: 43
aacaggtatc catagyttta                                                 20

<210> SEQ ID NO 44
<211> LENGTH: 22
<212> TYPE: DNA
<213> ORGANISM: Artificial Sequence
<220> FEATURE:
<223> OTHER INFORMATION: Protospacer
<220> FEATURE:
```

```
<221> NAME/KEY: misc_feature
<222> LOCATION: (20)..(20)
<223> OTHER INFORMATION: r is a or g

<400> SEQUENCE: 44
atgtttctgc tttcataaar ct                                              22

<210> SEQ ID NO 45
<211> LENGTH: 22
<212> TYPE: DNA
<213> ORGANISM: Artificial Sequence
<220> FEATURE:
<223> OTHER INFORMATION: Protospacer

<400> SEQUENCE: 45
tacacatatc aaaacaggta tc                                              22

<210> SEQ ID NO 46
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (10)..(10)
<223> OTHER INFORMATION: y is c or t

<400> SEQUENCE: 46
caggagaaty gcttgaaccc                                                 20

<210> SEQ ID NO 47
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (7)..(7)
<223> OTHER INFORMATION: y is c or t

<400> SEQUENCE: 47
gagaatygct tgaaccctgg                                                 20

<210> SEQ ID NO 48
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (17)..(17)
<223> OTHER INFORMATION: y is c or t

<400> SEQUENCE: 48
gctgaagcag gagaatygct                                                 20

<210> SEQ ID NO 49
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (9)..(9)
<223> OTHER INFORMATION: y is c or t
```

```
<400> SEQUENCE: 49
aggagaatyg cttgaaccct                                               20

<210> SEQ ID NO 50
<211> LENGTH: 20
<212> TYPE: DNA
<213> ORGANISM: Artificial Sequence
<220> FEATURE:
<223> OTHER INFORMATION: Protospacer

<400> SEQUENCE: 50
ctccacctcc agggttcaag                                               20

<210> SEQ ID NO 51
<211> LENGTH: 20
<212> TYPE: DNA
<213> ORGANISM: Artificial Sequence
<220> FEATURE:
<223> OTHER INFORMATION: Protospacer

<400> SEQUENCE: 51
tccaaaggaa gaggcagcaa                                               20

<210> SEQ ID NO 52
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (17)..(17)
<223> OTHER INFORMATION: r is a or g

<400> SEQUENCE: 52
aaaagccaga aaaaacrtaa                                               20

<210> SEQ ID NO 53
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (16)..(16)
<223> OTHER INFORMATION: r is a or g

<400> SEQUENCE: 53
aaagccagaa aaacrtaaa                                                20

<210> SEQ ID NO 54
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (12)..(12)
<223> OTHER INFORMATION: y is c or t

<400> SEQUENCE: 54
tatccccttt aygttttttc                                               20

<210> SEQ ID NO 55
```

```
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (15)..(15)
<223> OTHER INFORMATION: r is a or g

<400> SEQUENCE: 55
aagccagaaa aaacrtaaag                                            20

<210> SEQ ID NO 56
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (14)..(14)
<223> OTHER INFORMATION: r is a or g

<400> SEQUENCE: 56
agccagaaaa aacrtaaagg                                            20

<210> SEQ ID NO 57
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (18)..(18)
<223> OTHER INFORMATION: r is a or g

<400> SEQUENCE: 57
aaaaagccag aaaaaacrta aa                                         22

<210> SEQ ID NO 58
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (13)..(13)
<223> OTHER INFORMATION: r is a or g

<400> SEQUENCE: 58
gccagaaaaa acrtaaaggg ga                                         22

<210> SEQ ID NO 59
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (15)..(15)
<223> OTHER INFORMATION: y is c or t

<400> SEQUENCE: 59
atcataaaga cttgytttcc                                            20
```

```
<210> SEQ ID NO 60
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (10)..(10)
<223> OTHER INFORMATION: r is a or g

<400> SEQUENCE: 60
tccaggaaar caagtcttta                                             20

<210> SEQ ID NO 61
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (14)..(14)
<223> OTHER INFORMATION: r is a or g

<400> SEQUENCE: 61
gtgttccagg aaarcaagtc tt                                          22

<210> SEQ ID NO 62
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (11)..(11)
<223> OTHER INFORMATION: y is c or t

<400> SEQUENCE: 62
tagtagttca yctatgttgc                                             20

<210> SEQ ID NO 63
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (10)..(10)
<223> OTHER INFORMATION: y is c or t

<400> SEQUENCE: 63
agtagttcay ctatgttgca                                             20

<210> SEQ ID NO 64
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (20)..(20)
<223> OTHER INFORMATION: r is a or g

<400> SEQUENCE: 64
tggaattcct gcaacatagr                                             20
```

```
<210> SEQ ID NO 65
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (11)..(11)
<223> OTHER INFORMATION: r is a or g

<400> SEQUENCE: 65
tgcaacatag rtgaactact                                               20

<210> SEQ ID NO 66
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (15)..(15)
<223> OTHER INFORMATION: r is a or g

<400> SEQUENCE: 66
ttcctgcaac atagrtgaac ta                                            22

<210> SEQ ID NO 67
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (13)..(13)
<223> OTHER INFORMATION: y is c or t

<400> SEQUENCE: 67
tctagtagtt cayctatgtt gc                                            22

<210> SEQ ID NO 68
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (18)..(18)
<223> OTHER INFORMATION: r is a or g

<400> SEQUENCE: 68
gaacctggta caaaacaraa                                               20

<210> SEQ ID NO 69
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (15)..(15)
<223> OTHER INFORMATION: r is a or g

<400> SEQUENCE: 69
cctggtacaa aacaraatga                                               20
```

```
<210> SEQ ID NO 70
<211> LENGTH: 22
<212> TYPE: DNA
<213> ORGANISM: Artificial Sequence
<220> FEATURE:
<223> OTHER INFORMATION: Protospacer

<400> SEQUENCE: 70
cattgtagaa cctggtacaa aa                                              22

<210> SEQ ID NO 71
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (22)..(22)
<223> OTHER INFORMATION: r is a or g

<400> SEQUENCE: 71
tgtagaacct ggtacaaaac ar                                              22

<210> SEQ ID NO 72
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (19)..(19)
<223> OTHER INFORMATION: r is a or g

<400> SEQUENCE: 72
agaacctggt acaaaacara at                                              22

<210> SEQ ID NO 73
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (13)..(13)
<223> OTHER INFORMATION: y is c or t

<400> SEQUENCE: 73
gctatcatca ttytgttttg ta                                              22

<210> SEQ ID NO 74
<211> LENGTH: 22
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (11)..(11)
<223> OTHER INFORMATION: r is a or g

<400> SEQUENCE: 74
gtacaaaaca raatgatgat ag                                              22

<210> SEQ ID NO 75
```

```
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (17)..(17)
<223> OTHER INFORMATION: y is c or t

<400> SEQUENCE: 75
tcccgaatag ctgggaytac                                           20

<210> SEQ ID NO 76
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (9)..(9)
<223> OTHER INFORMATION: r is a or g

<400> SEQUENCE: 76
ggcctgtart cccagctatt                                           20

<210> SEQ ID NO 77
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (8)..(8)
<223> OTHER INFORMATION: r is a or g

<400> SEQUENCE: 77
gcctgtartc ccagctattc                                           20

<210> SEQ ID NO 78
<211> LENGTH: 22
<212> TYPE: DNA
<213> ORGANISM: Artificial Sequence
<220> FEATURE:
<223> OTHER INFORMATION: Protospacer

<400> SEQUENCE: 78
ctgcttcagc atcccgaata gc                                        22

<210> SEQ ID NO 79
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (6)..(6)
<223> OTHER INFORMATION: w is a or t

<400> SEQUENCE: 79
tagatwatct cctgtcaaac                                           20

<210> SEQ ID NO 80
<211> LENGTH: 20
<212> TYPE: DNA
<213> ORGANISM: Artificial Sequence
```

```
<220> FEATURE:
<223> OTHER INFORMATION: Protospacer
<220> FEATURE:
<221> NAME/KEY: misc_feature
<222> LOCATION: (8)..(8)
<223> OTHER INFORMATION: w is a or t

<400> SEQUENCE: 80
aggagatwat ctatgtaaag                                           20

<210> SEQ ID NO 81
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (10)..(10)
<223> OTHER INFORMATION: w is a or t

<400> SEQUENCE: 81
acaggagatw atctatgtaa                                           20

<210> SEQ ID NO 82
<211> LENGTH: 22
<212> TYPE: DNA
<213> ORGANISM: Artificial Sequence
<220> FEATURE:
<223> OTHER INFORMATION: Protospacer

<400> SEQUENCE: 82
gacttatctc cctctttaca ta                                        22

<210> SEQ ID NO 83
<211> LENGTH: 20
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (18)..(18)
<223> OTHER INFORMATION: r is a or g

<400> SEQUENCE: 83
tttgaaggaa aggttttrta                                           20

<210> SEQ ID NO 84
<211> LENGTH: 21
<212> TYPE: DNA
<213> ORGANISM: Artificial Sequence
<220> FEATURE:
<223> OTHER INFORMATION: Protospacer
<220> FEATURE:
<221> NAME/KEY: misc_feature
<222> LOCATION: (21)..(21)
<223> OTHER INFORMATION: r is a or g

<400> SEQUENCE: 84
agatttgaag gaaaggtttt r                                         21

<210> SEQ ID NO 85
<211> LENGTH: 20
<212> TYPE: DNA
<213> ORGANISM: Artificial Sequence
<220> FEATURE:
<223> OTHER INFORMATION: Protospacer
```

```
<400> SEQUENCE: 85
tttgaaggaa aggttttgta                                               20

<210> SEQ ID NO 86
<211> LENGTH: 21
<212> TYPE: DNA
<213> ORGANISM: Artificial Sequence
<220> FEATURE:
<223> OTHER INFORMATION: Protospacer

<400> SEQUENCE: 86
agatttgaag gaaaggtttt g                                             21

<210> SEQ ID NO 87
<211> LENGTH: 20
<212> TYPE: DNA
<213> ORGANISM: Artificial Sequence
<220> FEATURE:
<223> OTHER INFORMATION: Protospacer

<400> SEQUENCE: 87
tttgaaggaa aggttttgta                                               20

<210> SEQ ID NO 88
<211> LENGTH: 21
<212> TYPE: DNA
<213> ORGANISM: Artificial Sequence
<220> FEATURE:
<223> OTHER INFORMATION: Protospacer

<400> SEQUENCE: 88
agatttgaag gaaaggtttt g                                             21
```